US011090247B2

(12) United States Patent
Goo et al.

(10) Patent No.: US 11,090,247 B2
(45) Date of Patent: Aug. 17, 2021

(54) COMPOSITIONS FOR PROTECTING THE SKIN FROM HEAVY METALS AND FORMALDEHYDE

(71) Applicant: FNG RESEARCH CO., LTD., Cheongju-si (KR)

(72) Inventors: Young Sam Goo, Hongseong-gun (KR); Ki Nam Son, Cheongju-si (KR)

(73) Assignee: FNG RESEARCH CO., LTD., Cheongju-si (KR)

( * ) Notice: Subject to any disclaimer, the term of this patent is extended or adjusted under 35 U.S.C. 154(b) by 0 days.

(21) Appl. No.: 16/464,209

(22) PCT Filed: Jun. 2, 2017

(86) PCT No.: PCT/KR2017/005821
§ 371 (c)(1),
(2) Date: May 24, 2019

(87) PCT Pub. No.: WO2018/097431
PCT Pub. Date: May 31, 2018

(65) Prior Publication Data
US 2019/0388323 A1   Dec. 26, 2019

(30) Foreign Application Priority Data

Nov. 25, 2016 (KR) .................. 10-2016-0157956
Feb. 28, 2017 (KR) .................. 10-2017-0026114

(51) Int. Cl.
*A61K 8/49* (2006.01)
*A61K 8/44* (2006.01)
*A61Q 19/00* (2006.01)

(52) U.S. Cl.
CPC .............. *A61K 8/4926* (2013.01); *A61K 8/44* (2013.01); *A61K 8/445* (2013.01); *A61K 8/4973* (2013.01); *A61Q 19/00* (2013.01)

(58) Field of Classification Search
CPC . A61K 8/41; A61K 8/44; A61K 8/445; A61K 8/4926; A61K 8/494; A61K 8/4973; A61Q 17/00; A61Q 19/00; C07C 229/24; C07C 229/26; C07C 229/60; C07D 213/80; C07D 257/02; C07D 307/68; C07D 401/14; C07D 407/14
See application file for complete search history.

(56) References Cited

U.S. PATENT DOCUMENTS

| 2005/0209120 A1* | 9/2005 | Reinhardt | C11D 3/3932 |
| | | | 510/312 |
| 2010/0210451 A1* | 8/2010 | Busch | B01J 31/182 |
| | | | 502/155 |
| 2011/0206630 A1* | 8/2011 | Rude | C11D 1/72 |
| | | | 424/70.12 |

* cited by examiner

*Primary Examiner* — Savitha M Rao
(74) *Attorney, Agent, or Firm* — Birch, Stewart, Kolasch & Birch, LLP

(57) ABSTRACT

The present invention provides a composition for protecting the skin from heavy metals and formaldehyde, comprising at least one selected from the group consisting of trientine or trientine derivative of Formula (1), cyclen or cyclen derivative of Formula (2), cyclam or cyclam derivative of Formula (3), and a salt thereof.

4 Claims, 4 Drawing Sheets

[Fig. 1]
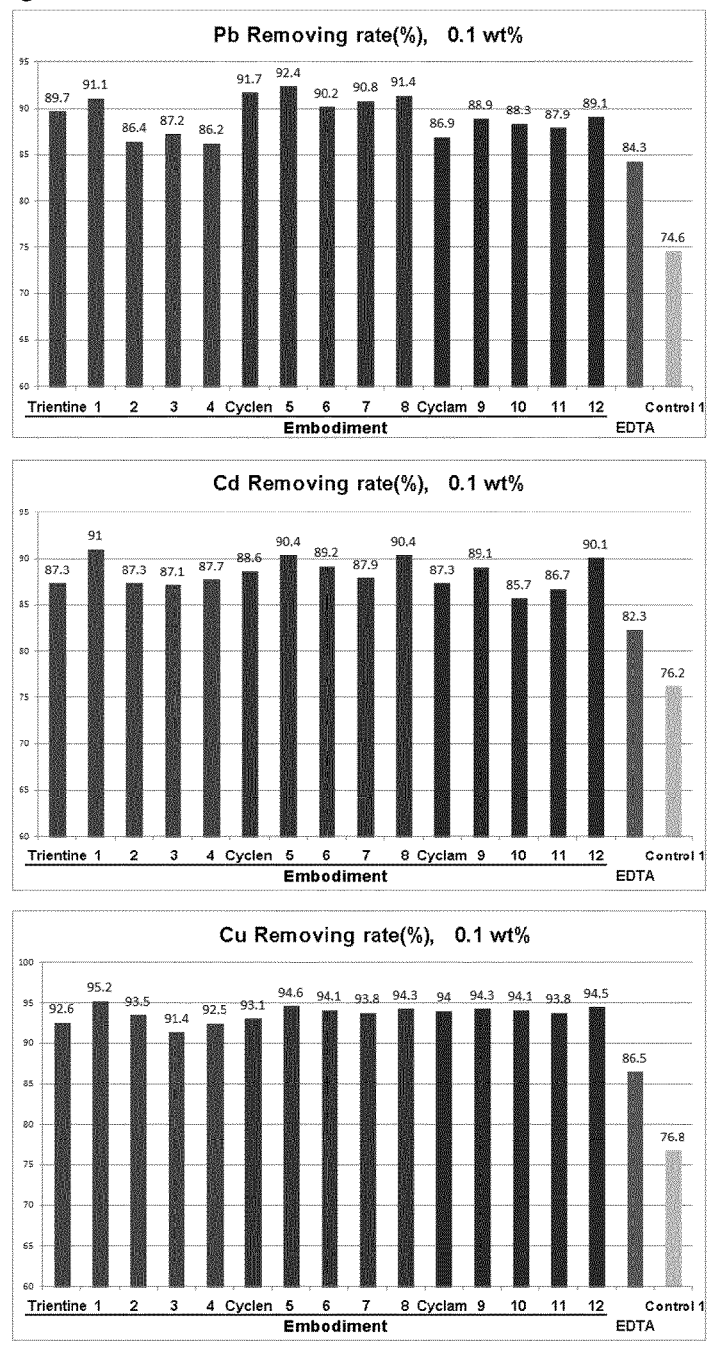

[Fig. 2]
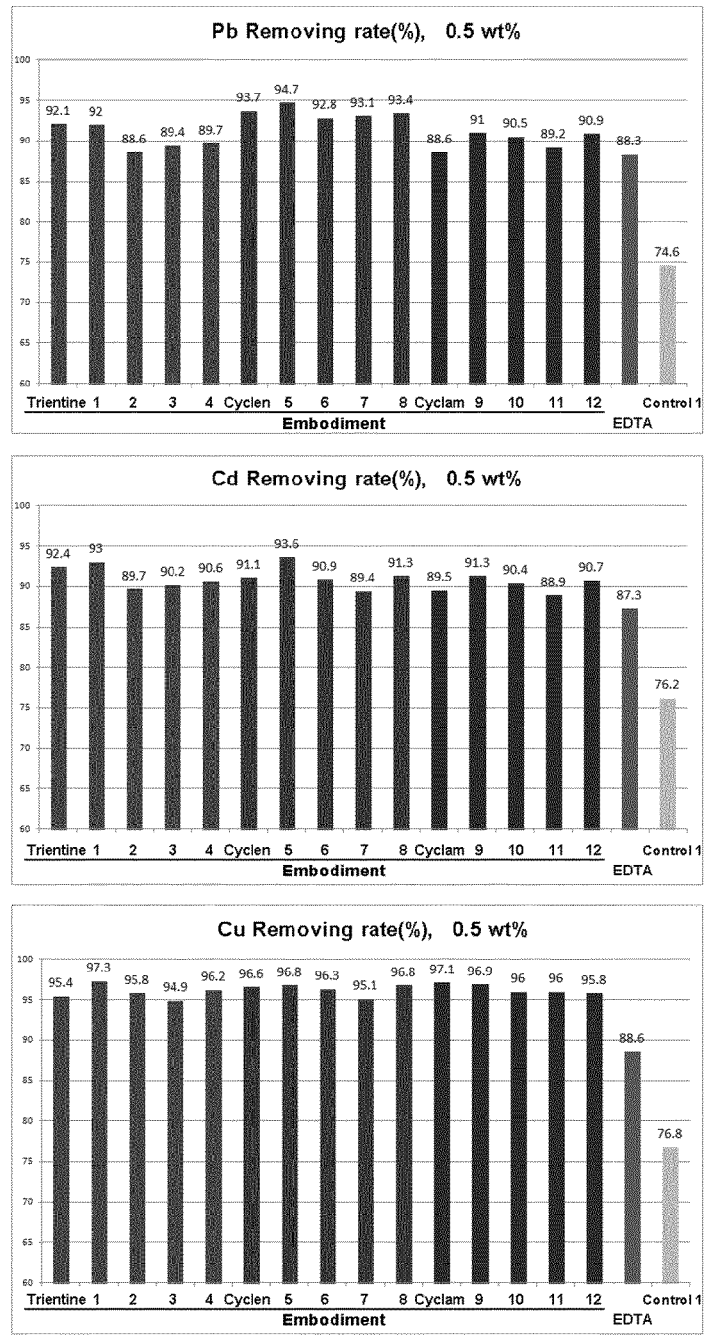

[Fig. 3]
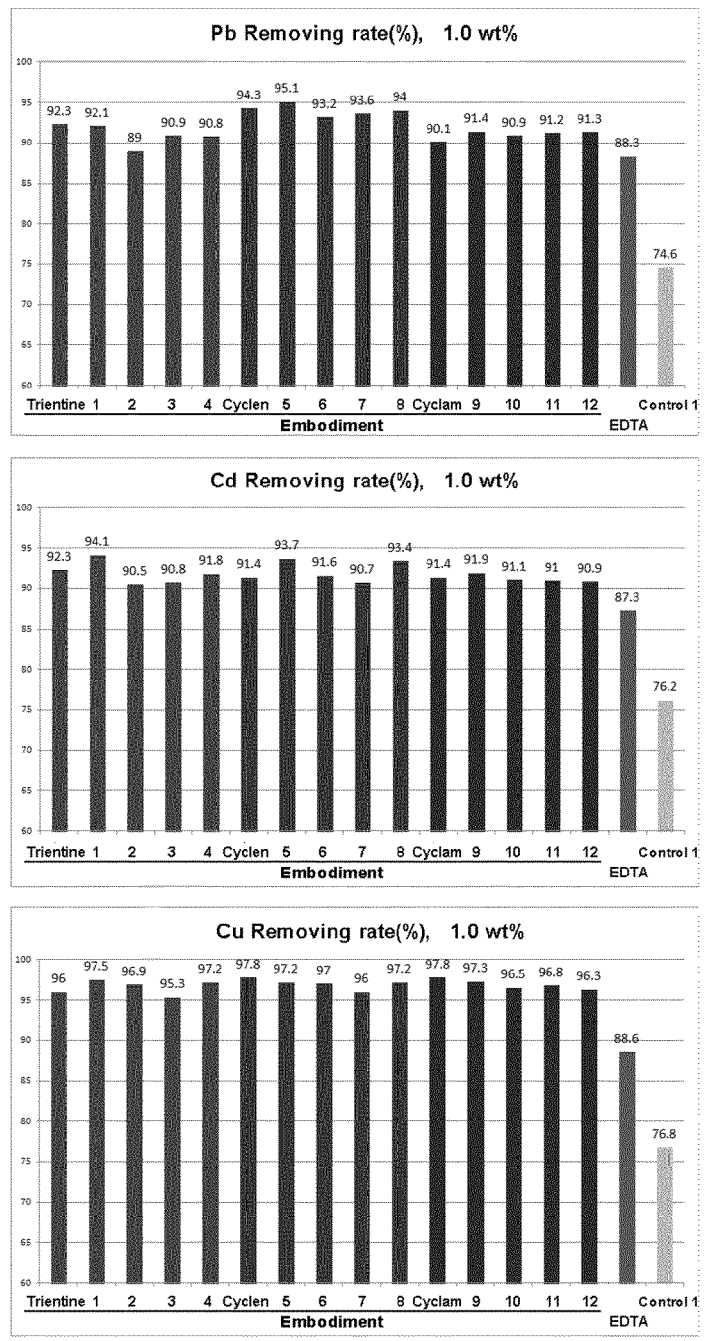

[Fig. 4]
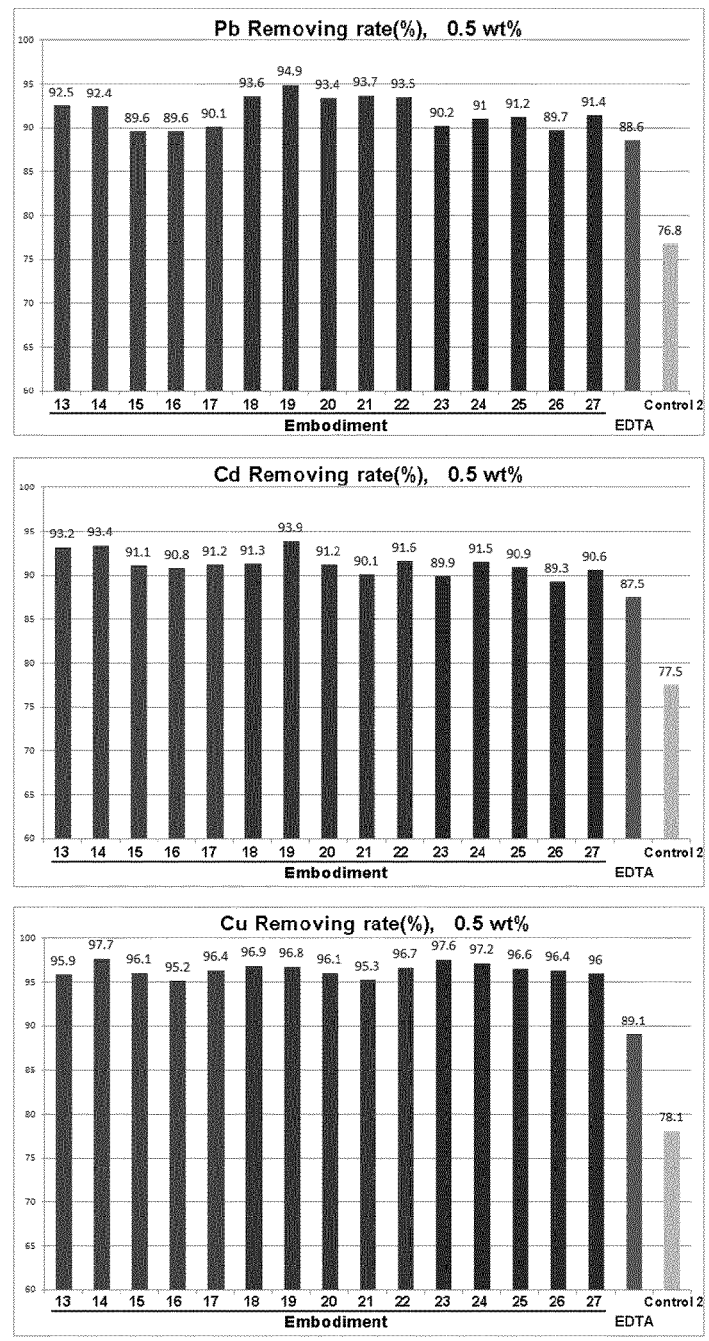

COMPOSITIONS FOR PROTECTING THE SKIN FROM HEAVY METALS AND FORMALDEHYDE

CROSS REFERENCE TO RELATED APPLICATIONS

This application is the National Phase of PCT/KR2017/005821 filed on Jun. 2, 2017, which claims priority under 35 U.S.C. § 119(a) to Patent Application Nos. 10-2016-0157956 and 10-2017-0026114 filed in the Republic of Korea on Nov. 25, 2016 and Feb. 28, 2017, respectively, all of which are hereby expressly incorporated by reference into the present application.

TECHNICAL FIELD

The present invention relates to compositions for protecting the skin from the external environment. In particular, the present invention relates to compositions for effectively removing heavy metals and formaldehyde attached or absorbed on the skin.

BACKGROUND ART

Air pollution is getting worse with industrial development. Major air pollutants are volatile organic compounds (VOCs) such as formaldehyde, harmful gases such as sulfur dioxide, nitrogen oxides, ozone and carbon monoxide, and heavy metals such as Pb, Cd, As, Cr, Cu, Ni. These pollutants are commonly absorbed or condensed into fine dusts ($PM_{10}$) or ultrafine dusts ($PM_{2.5}$), and enter into the body through the respiratory tract, thereby causing various respiratory diseases such as asthma and lung function deterioration. Also these pollutants cause various skin diseases such as dermatitis, allergy, atopy and the like.

Formaldehyde is a representative VOC which is classified as carcinogenic to humans, and is well known as the atopy-inducing substance.

Although the components of fine dusts depend on area, environment and season, it has been reported that harmful heavy metals such as Hg, Pb, Cd, As, Cr, Cu, Ni, Zn, Mn, Co and Sn are contained in the fine dust in an amount of about 20 wt %.

Various compositions in the form of cosmetics are disclosed to protect the skin from fine dusts and heavy metals.

Korean Patent Publication No. 10-2010-0056239 discloses a cosmetic composition comprising at least one more selected from the group consisting of a mushroom polysaccharide, a seaweed polysaccharide, and a *ginseng* polysaccharide as an active ingredient to absorb the heavy metals in dust storm, exhaust gas, external contaminants and fine dusts.

Korean Patent Registration No. 10-0715241 discloses a cosmetic composition comprising carboxylated alginic acid, which is prepared by treating alginic acid with hydrogen peroxide, as an active ingredient for cleaning heavy metals.

Korean Patent Publication No. 10-2016-0000959 discloses a cosmetic composition for removing heavy metals and fine dusts, comprising lees (residue left after rice liquor is drained) as an active ingredient, which is a by-product produced in a liquor manufacturing process such as rice liquor.

Ethylenediaminetetraacetic acid (EDTA) is an ethylenediamine compound that binds to metal ions with four carboxyl groups and two amine groups, so that it forms a water-soluble chelate compound. Since EDTA has a strong affinity with $Pb^{2+}$, it is pharmaceutically used as a treatment for lead poisoning. In relation to cosmetics, EDTA is mainly used as a sequestering agent for $Ca^{2+}$ and $Mg^{2+}$ contained in cosmetics to increase the stability of cosmetics and also is used as a component for moisturizing skin. Although EDTA is an effective chelating agent for heavy metal ions, since it is known to cause skin irritation, it is usually used in an amount of 0.05 wt % or less based on the total weight of the cosmetics, and not more than 0.10 wt % is usually not used.

DISCLOSURE OF INVENTION

Technical Problem

It is an object of the present invention to provide a composition for a skin having a high metal and formaldehyde removing ability, wherein skin irritation and toxicity is free or extremely low, in comparison with conventional materials.

Solution to Problem

The present invention provides a composition for protecting the skin from heavy metals and formaldehyde, comprising at least one selected from the group consisting of trientine or trientine derivative of Formula (1), cyclen or cyclen derivative of Formula (2), cyclam or cyclam derivative of Formula (3), and a salt thereof.

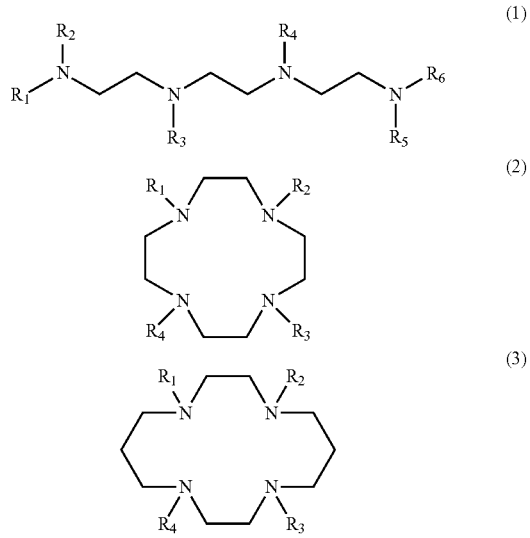

wherein: $R_1$, $R_2$, $R_3$, $R_4$, $R_5$ and $R_6$ is each independently hydrogen, —$R_7$—COOH;

$R_7$ is a $C_1$-$C_5$ alkyl group, an unsubstituted or substituted aromatic hydrocarbon group, or an unsubstituted or substituted aromatic heterocyclic group.

In the present invention, the effective ingredient for protecting the skin from heavy metals and formaldehyde is preferably selected from trientine of Formula (1a), cyclen of Formula (2a), and cyclam of Formula (3a).

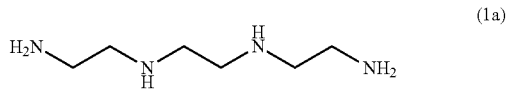

-continued (2a)

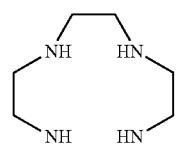

The trientine derivative is preferably selected from compounds of Formula (1b) to (1d) or a salt thereof.

(3a)

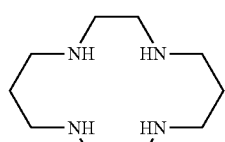

(1b)

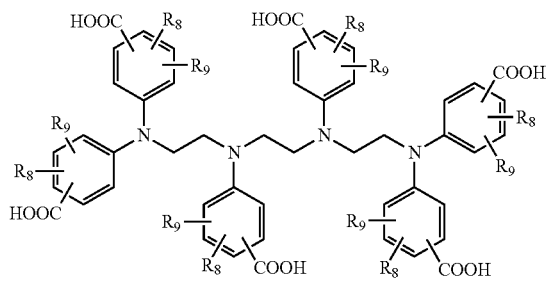

(1c)

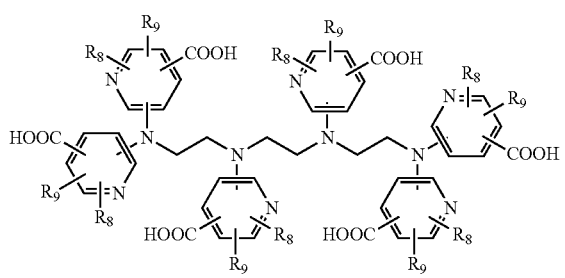

(1d)

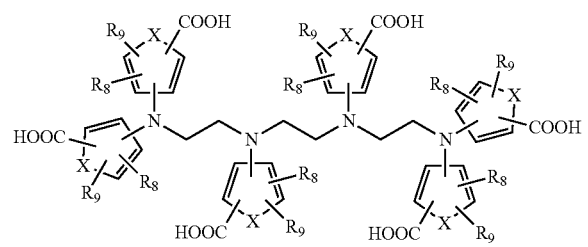

wherein: $R_8$, $R_9$ is each independently hydrogen or $C_1$-$C_4$ alkyl;

X is oxygen, sulfur or nitrogen atom.

The cyclen derivative is preferably selected from compounds of Formula (2b) to (2d) or a salt thereof.

(2b)

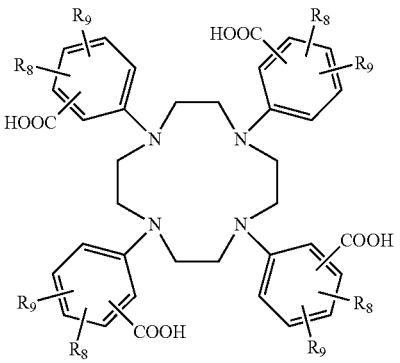

(2c)

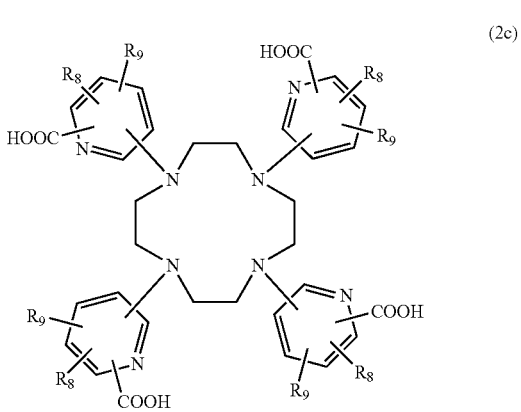

(2d)

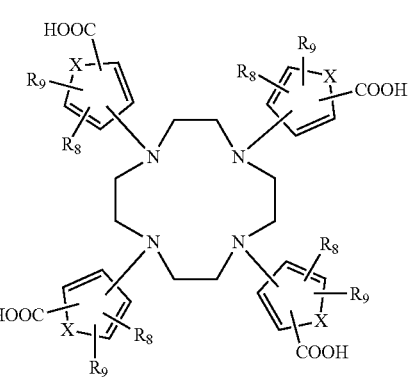

wherein: $R_8$, $R_9$ is each independently hydrogen or $C_1$-$C_4$ alkyl;

X is oxygen, sulfur or nitrogen atom.

The cyclam derivative is preferably selected from compounds of Formula (3b) to (3d) or a salt thereof.

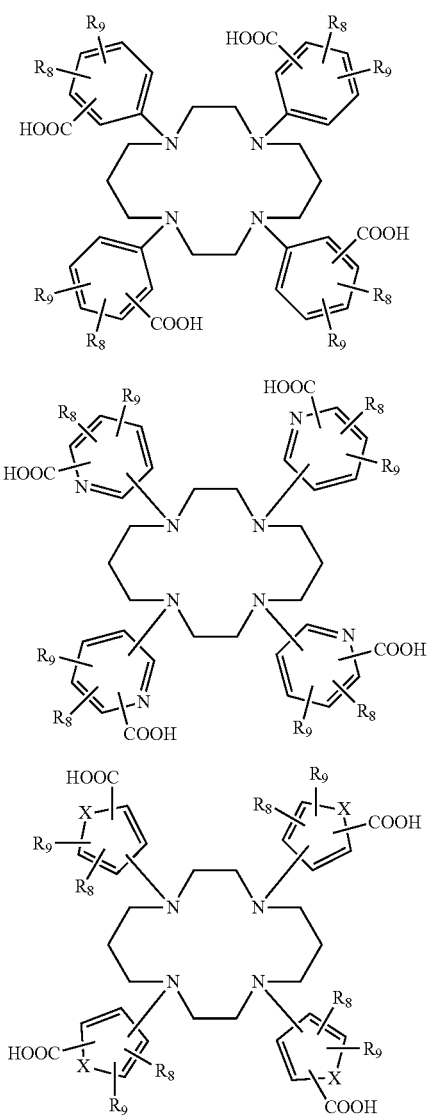

wherein: $R_8$, $R_9$ is each independently hydrogen or $C_1$-$C_4$ alkyl;

X is oxygen, sulfur or nitrogen atom.

Advantageous Effects of Invention

The composition for skin of the present invention has an effect of eliminating formaldehyde and has strong heavy metal removal ability even in a small amount in comparison with the conventional chelating agent. On the other hand, the composition for skin of the present invention has no or little skin irritation and toxicity, and thus can be effectively used as a skin composition for protecting skin from external environment.

BRIEF DESCRIPTION OF DRAWINGS

FIG. 1 is a graph showing the heavy metal removal ability of 0.1 wt % aqueous solution of compounds according to Embodiments 1 to 12.

FIG. 2 is a graph showing the heavy metal removal ability of 0.5 wt % aqueous solution of compounds according to Embodiments 1 to 12.

FIG. 3 is a graph showing the heavy metal removal ability of 1.0 wt % aqueous solution of compounds according to Embodiments 1 to 12.

FIG. 4 is a graph showing the heavy metal removal ability of 0.5 wt % compositions for skin according to Embodiments 13 to 27.

BEST MODE FOR CARRYING OUT THE INVENTION

The inventors of the present invention have conducted various studies on heavy metal chelating agents in order to develop a composition for a skin that can effectively remove heavy metals attached or absorbed on the skin induced by exposure to an external pollution environment.

Trientine of the following Formula (1a) is a generic name of Triethylenetetramine (TETA).

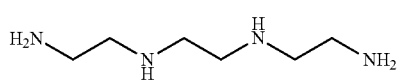
(1a)

Triethylenetetramine dihydrochloride has been shown to participate in the metabolism of copper in mouse experiments (F. W. Sunderman et al., *Toxicol. Appl. Pharmacol.* 38, 177 (1976)). Triethylenetetramine dihydrochloride is pharmacologically well known as a chelating agent for copper, so is well known as a treatment for Wilson's disease (J M Walshe, *Prog. Clin. Biol. Res.* 34, 271 (1979); R H Haslam et al., *Dev. Pharmacol Ther.* 1, 318 (1980)).

Cyclen of the following Formula (2a) is a generic name of 1,4,7,10-tetraazacyclododecane. It forms a chelate through coordination bond with gadolinium (Gd) and is used for nuclear medical contrast agent.

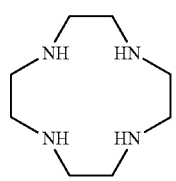
(2a)

Cyclam of the following Formula (3a) is a generic name of 1,4,8,11-tetraazacyclotetradecane. It also forms a chelate through coordination bond with gadolinium (Gd) and is used for nuclear medical contrast agent.

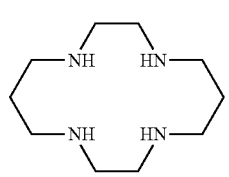
(3a)

Chelating agents such as trientine, cyclen and cyclam, are pharmaceutically well known for their ability to release copper in the body via oral or vascular administration methods, or use thereof as a contrast agent. However, these have not been reported for use for protecting skin such as removal of heavy metals on the skin.

The present invention discloses trientine, cyclen, cyclam and derivatives thereof is very useful in the removal of heavy metals from the skin, as well as skin irritation and toxicity. Trientine, cyclen and cyclam are known to be harmful to the skin in the past. As a result of the experiments of the present invention, it has been found that the use of an effective amount for removing heavy metals on the skin does not cause skin irritation and toxicity so that it can be acceptable as ingredients for protecting skin.

On the other hand, it is disclosed by the present invention that trientine, cyclen, cyclam and derivatives thereof are very effective for the removal of formaldehyde which is a primary carcinogen.

The present invention provides a composition for protecting the skin from heavy metals and formaldehyde, comprising at least one selected from the group consisting of trientine or trientine derivative of Formula (1), cyclen or cyclen derivative of Formula (2), cyclam or cyclam derivative of Formula (3), and a salt thereof.

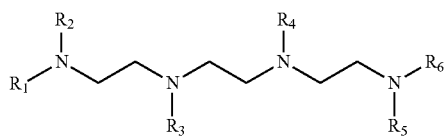

(1)

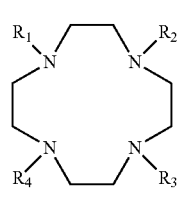

(2)

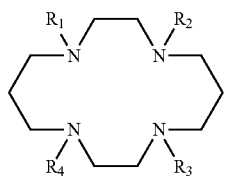

(3)

wherein: $R_1$, $R_2$, $R_3$, $R_4$, $R_5$ and $R_6$ is each independently hydrogen, —$R_7$—COOH;

$R_7$ is a $C_1$-$C_5$ alkyl group, an unsubstituted or substituted aromatic hydrocarbon group, or an unsubstituted or substituted aromatic heterocyclic group.

The composition for skin of the present invention is characterized in that it comprises trientine, trientine derivatives, cyclen, cyclen derivatives, cyclam, cyclam derivatives or a salt thereof as an effective ingredient for removing heavy metals and formaldehyde on the skin.

On the other hand, in the present invention, it is confirmed that the introduction of a carboxyl group at the amine position of trientine, cyclen and cyclam improves the degree of coordination of heavy metal, while the introduction of an aromatic or heterocyclic group at the amine position significantly reduces skin irritation.

The trientine derivatives, cyclen derivatives and cyclam derivatives according to the present invention are preferably selected from the compounds of the following Formulas (1b) to (3d).

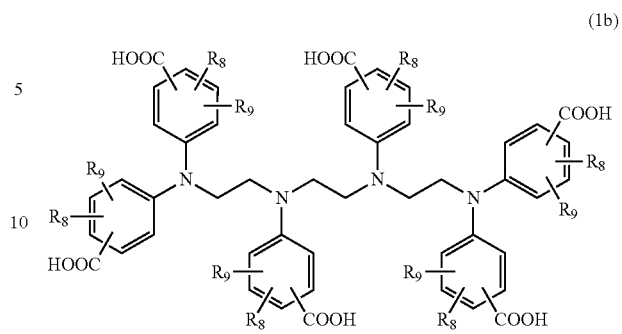

(1b)

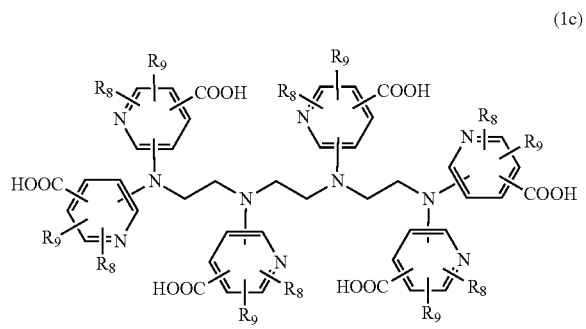

(1c)

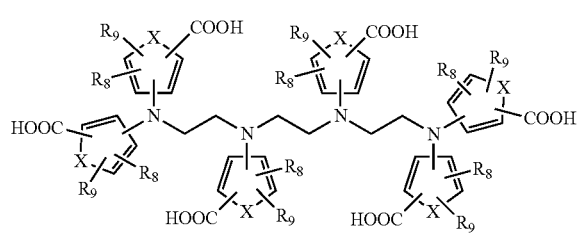

(1d)

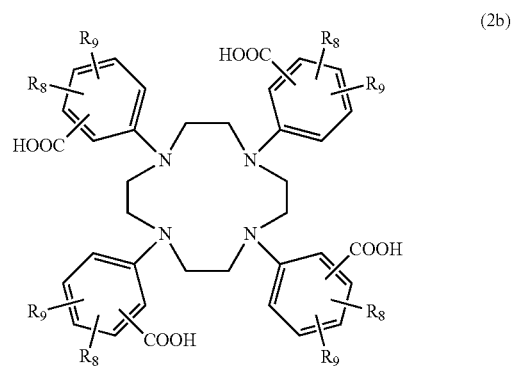

(2b)

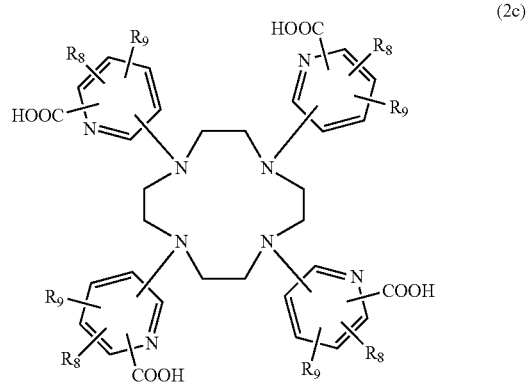

(2c)

-continued (2d)
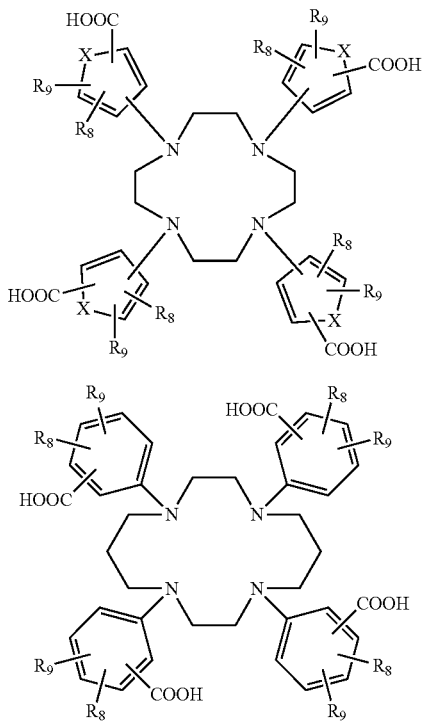

(3b)

(3c)
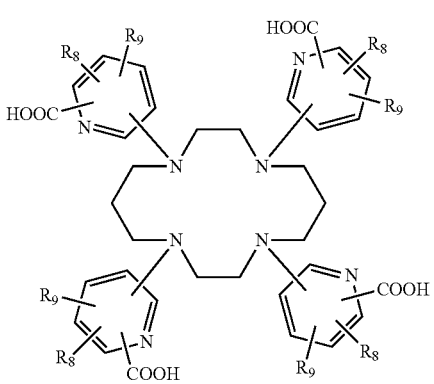

(3d)
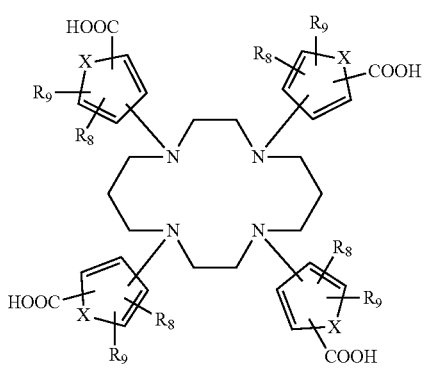

wherein: $R_8$, $R_9$ is each independently hydrogen or $C_1$-$C_4$ alkyl;

X is oxygen, sulfur or nitrogen atom.

The trientine or trientine derivatives, cyclen or cyclen derivatives, cyclam or cyclam derivatives of the present invention is not limited to but 0.01 to 5.0 wt %, preferably 0.05 to 2.0 wt %, more preferably 0.1 to 1.0 wt %, based a total weight of the composition.

The trientine or trientine derivatives, cyclen or cyclen derivatives, cyclam or cyclam derivatives of the present invention may be used in the form of water-soluble salts. The said compounds of the present invention may be used in the form of the hydrochloride salt, the sodium salt, and the potassium salt. The said salts of the present invention can be obtained by a known method for preparing the salts. The salt of the present invention is preferably dihydrochloride or tetrahydrochloride, more preferably dihydrochloride.

The composition of the present invention can be used for removing heavy metal ions such as Hg, Pb, Cd, As, Cr, Cu, Ni, Zn, Mn, Co and Sn which be attached, absorbed on the skin.

The composition for a skin according to the present invention can be formulated into an oil-in-water (O/W) emulsion or water-in-oil (W/O) emulsion or an oil-free emulsion. The composition for a skin according to the present invention can be used for cosmetics such as basic cosmetics, makeup cosmetics, cleansing cosmetics, shampoo, soap and so on. Formulations of compositions of the present invention may be soft lotion, nutritional lotion, nutritional essence, nutritional oil, moisturizing oil, nutritional cream, moisturizing cream, powder, pack, foundation, makeup base, stick, cleansing, shampoo, gel, lotion and ointment. The composition for a skin according to the present invention may be used in various forms such as liquid, cream, paste, and solid, and may be formulated using conventional cosmetic preparation methods.

The composition for skin of the present invention may further comprise a known cosmetic ingredient necessary for the above-mentioned formulation, for example, preservatives, antimicrobial agents, antioxidants, plant extracts, pH adjusters, alcohols, pigments, fragrances, blood circulation accelerators, coolants, purified water and ionized water.

On the other hand, the composition for skin of the present invention can be used as a pharmaceutical auxiliary ingredient for hair loss treatment or skin related treatment by effective removal of heavy metals on the skin.

Hereinafter, the composition for skin having a heavy metal and formaldehyde removing ability according to the present invention will be described in detail with reference to the following examples. However, the following examples are only illustrative of the present invention and are not to be construed as limiting the scope of the present invention.

MODE FOR THE INVENTION

Synthesis of Trientine Derivative

Embodiment 1

Preparation of 3,6,9,12-tetrakis(carboxymethyl)-3,6,9,12-tetraazatetradecanedioic acid (Formula (1e))

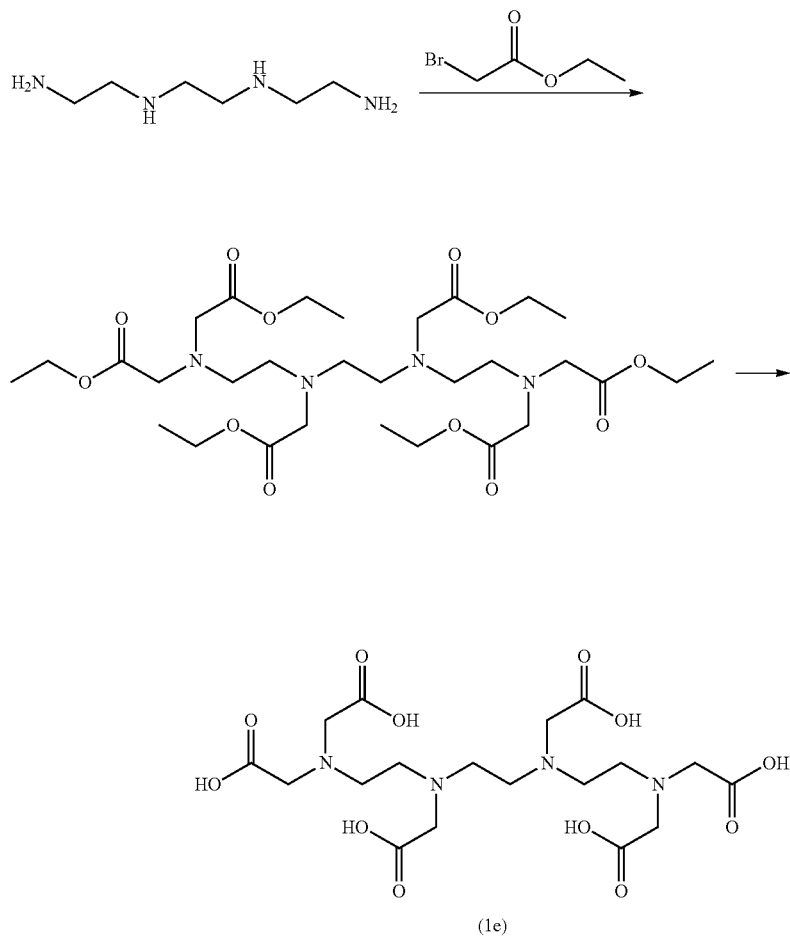

(1e)

Triethylenetetramine (10.0 g) was dissolved in acetonitrile (ACN) (400 ml). $K_2CO_3$ (66.1 g) and ethyl bromoacetate (78.8 g) were added and reaction mixture was heated under stirring and under reflux for about 48 hours. After completion of the reaction, the reaction mixture was cooled to room temperature, and then filtered. A solid phase of the reaction mixture was discarded and the filtrate was concentrated under vacuum. Methylene chloride (MC) (200 ml) and purified water (300 ml) are added to the concentrate and stirred for 30 min, and then an organic layer is separated. The organic layer was treated with $MgSO_4$, concentrated under vacuum, and then subjected to column purification with MC-methanol. 29.6 g of diethyl 3,6,9,12-tetrakis(2-ethoxy-2-oxoethyl)-3,6,9,12-tetraazatetradecanedioate was obtained (Yield: 64.8%).

$^1$H NMR (CDCl$_3$): 4.16 (q, 8H), 4.14 (q, 4H), 3.57 (s, 8H), 3.44 (s, 4H), 2.85 (t, 4H), 2.78 (t, 4H), 2.74 (s, 4H), 1.27 (t, 12H), 1.26 (t, 6H)

Diethyl 3,6,9,12-tetrakis (2-ethoxy-2-oxoethyl)-3,6,9,12-tetraazatetradecanedioate (29.6 g), NaOH (12.33 g), methanol (180 ml) and purified water (120 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (400 ml). The extracted organic layer was treated with MgSO$_4$. 15.9 g of the title compound was obtained (Yield: 72.3%).

$^1$H NMR (DMSO): 4.57 (s, 8H), 4.55 (s, 4H), 4.22 (s, 12H)

Embodiment 2

Preparation of 4,4',4'',4'''-(((ethane-1,2-diylbis((4-carboxyphenyl)azanediyl))bis(ethane-2,1-diyl))bis(azanetriyl))tetrabenzoic acid (Formula (1f))

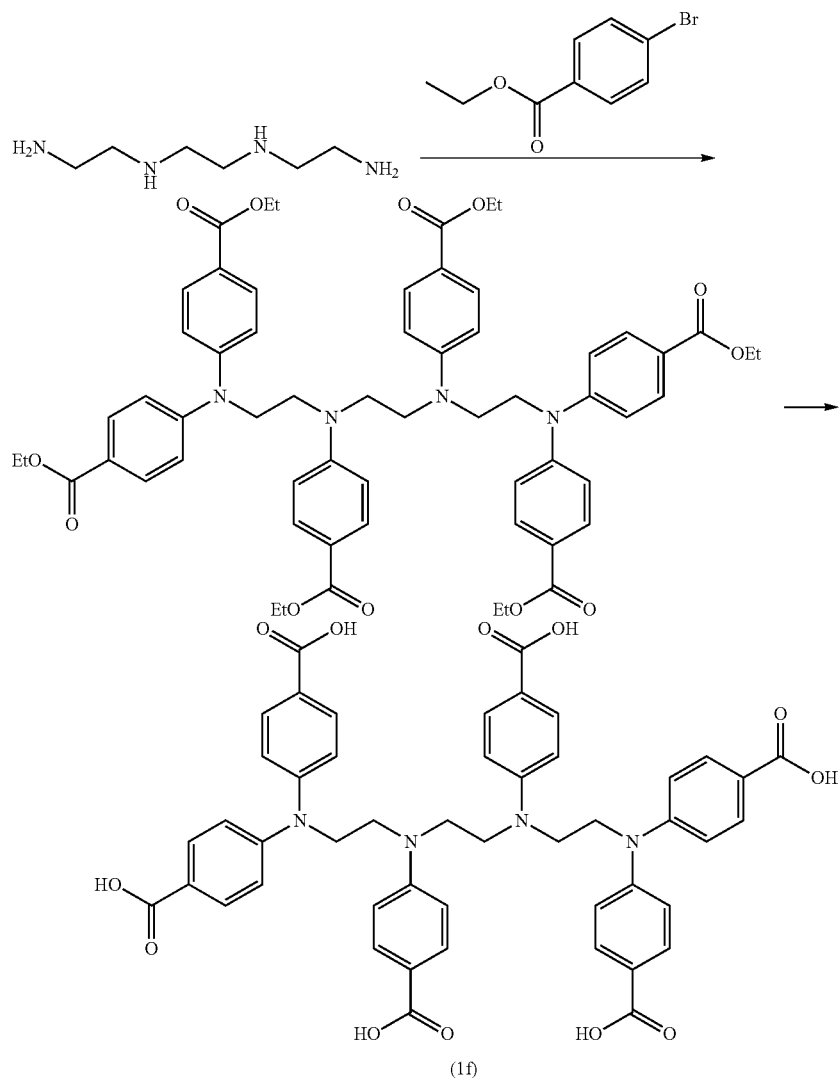

(1f)

Triethylenetetramine (10.0 g), ethyl 4-bromobenzoate (108.1 g), t-BuONa (46.0 g) and toluene (600 ml) were added, stirred, and then heated to 35° C. 50% (t-Bu)$_3$P toluene solution (2.8 g) was added, stirred for about 30 min and then heated to 50° C. Pd(dba)$_2$ (Bis(dibenzylideneacetone)palladium) (2.0 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO$_4$, concentrated under vacuum, and then subjected to column purification with MC-methanol. 22.9 g of tetraethyl 4,4',4'',4'''-(((ethane-1,2-diylbis((4-(ethoxycarbonyl)phenyl)azanediyl)) bis(ethane-2,1-diyl))bis(azanetriyl))tetrabenzoate was obtained (Yield: 32.4%)

$^1$H NMR (CDCl$_3$): 7.82 (m, 4H), 7.71 (m, 8H), 7.25 (m, 8H), 6.95 (m, 4H), 4.15 (q, 8H), 4.11 (q, 4H), 3.45~3.18 (m, 12H), 1.27 (t, 12H), 1.26 (t, 6H)

Tetraethyl 4,4',4'',4'''-(((ethane-1,2-diylbis((4-(ethoxycarbonyl)phenyl)azanediyl)) bis(ethane-2,1-diyl))bis(azanetriyl))tetrabenzoate (22.9 g), NaOH (6.1 g), methanol (180 ml) and purified water (140 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (200 ml). The extracted organic layer was treated with MgSO₄. 17.0 g of the title compound was obtained (Yield: 89.0%).

¹H NMR (DMSO): 7.80 (m, 4H), 7.68 (m, 8H), 7.15 (m, 8H), 6.94 (m, 4H), 3.41~3.28 (m, 12H)

Embodiment 3

Preparation of 5,5'-((2-((5-carboxypyridin-3-yl)(2-((5-carboxypyridin-3-yl)(2-((5-carboxypyridin-3-yl)(2-carboxypyridin-4-yl)amino)ethyl)amino)ethyl)amino)ethyl)azanediyl)dinicotinic acid (Formula (1g))

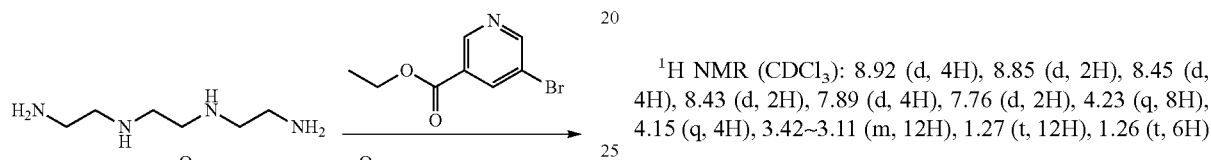

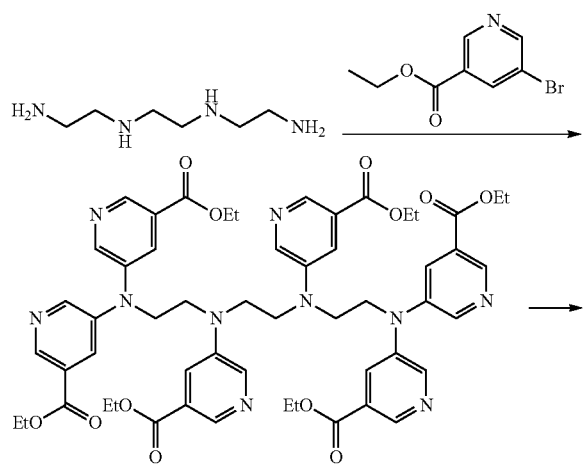

(1g)

Triethylenetetramine (10.0 g), ethyl 5-bromonicotinate (108.5 g), t-BuONa (46.0 g) and xylene (600 ml) were added, stirred, and then heated to 35° C. 50% (t-Bu)₃P toluene solution (2.8 g) was added, stirred for about 30 min and then heated to 50° C. Pd(dba)₂ (2.0 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO₄, concentrated diethyl 5,5'-((2-((5-(ethoxycarbonyl)pyridin-3-yl)(2-((5-(ethoxycarbonyl)pyridin-3-yl)(2-((5-(e thoxycarbonyl)pyridin-3-yl)(2-(ethoxycarbonyl)pyridin-4-yl)amino) ethyl)amino)ethyl) amino)ethyl)azanediyl)dinicotinate was obtained (Yield: 27.8%).

¹H NMR (CDCl₃): 8.92 (d, 4H), 8.85 (d, 2H), 8.45 (d, 4H), 8.43 (d, 2H), 7.89 (d, 4H), 7.76 (d, 2H), 4.23 (q, 8H), 4.15 (q, 4H), 3.42~3.11 (m, 12H), 1.27 (t, 12H), 1.26 (t, 6H)

Diethyl 5,5'-((2-((5-(ethoxycarbonyl)pyridin-3-yl)(2-((5-(ethoxycarbonyl)pyridin 3-yl)(2-((5-(ethoxycarbonyl)pyridin-3-yl)(2-(ethoxycarbonyl)pyridin-4-yl)amino)ethyl) amino)ethyl)amino)ethyl)azanediyl)dinicotinate (19.8 g), NaOH (5.3 g), methanol (160 ml) and purified water (120 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (160 ml). The extracted organic layer was treated with MgSO₄. 13.0 g of the title compound was obtained (Yield: 78.4%).

¹H NMR (DMSO): 8.95 (d, 4H), 8.87 (d, 2H), 8.46 (d, 4H), 8.44 (d, 2H), 7.89 (d, 4H), 7.75 (d, 2H), 3.41~3.11 (m, 12H)

Embodiment 4

Preparation of 5,5',5'',5'''-((((ethane-1,2-diylbis((5-carboxyfuran-2-yl)azanediyl))bis(ethane-2,1-di yl))bis(azanetriyl))tetrakis(furan-2-carboxylic acid) (Formula (1h))

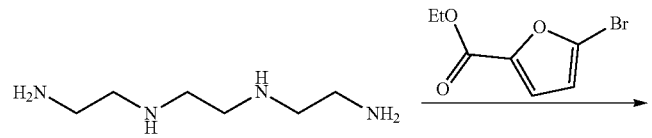

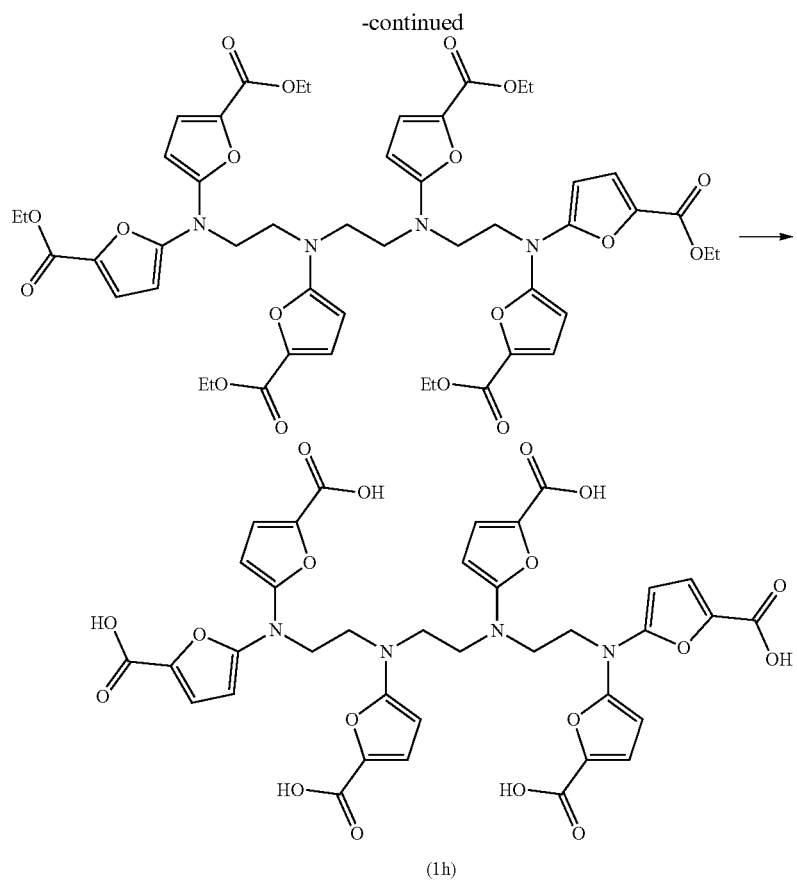

(1h)

Triethylenetetramine (10.0 g), ethyl 5-bromofuran-2-carboxylate (103.3 g), t-BuONa (46.0 g) and toluene (600 ml) were added, stirred, and then heated to 35° C. 50% (t-Bu)$_3$P toluene solution (2.8 g) was added, stirred for about 30 min and then heated to 50° C. Pd(dba)$_2$ (2.0 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO$_4$, concentrated under vacuum, and then subjected to column purification with MC-methanol. 25.3 g of tetraethyl 5,5',5",5'''-(((ethane-1,2-diylbis((5-(ethoxycarbonyl)furan-2-yl)azanediyl))bis(ethane-2,1-diyl))bis(azanetriyl))tetrakis(furan-2-carboxylate) was obtained (Yield: 37.9%).

$^1$H NMR (CDCl$_3$): 7.42 (m, 12H), 4.31 (q, 8H), 4.28 (q, 4H), 3.65~3.15 (m, 12H), 1.27 (t, 12H), 1.25 (t, 6H)

Tetraethyl 5,5',5",5'''-(((ethane-1,2-diylbis((5-(ethoxycarbonyl)furan-2-yl)azanediyl))bis (ethane-2,1-diyl))bis(azanetriyl))tetrakis(furan-2-carboxylate) (25.3 g), NaOH (7.2 g), methanol (200 ml) and purified water (150 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (200 ml). The extracted organic layer was treated with MgSO$_4$. 15.0 g of the title compound was obtained (Yield: 71.8%).

$^1$H NMR (DMSO): 7.41 (m, 12H), 3.67~3.15 (m, 12H)

Synthesis of Cyclen Derivative

Embodiment 5

Preparation of 2,2',2",2'''-(1,4,7,10-tetraazacyclododecane-1,4,7,10-tetrayl)tetraacetic acid (Formula (2e))

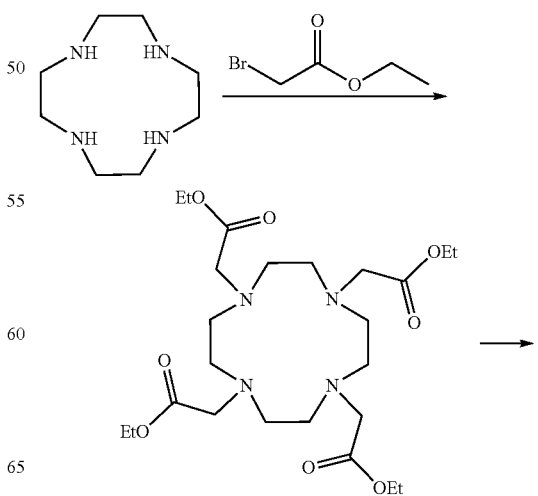

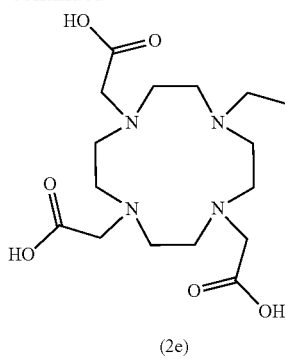

(2e)

Cyclen (10.0 g) was dissolved in acetonitrile (400 ml). K₂CO₃ (40.1 g) and ethyl bromoacetate (42.7 g) were added and reaction mixture was heated under stirring and under reflux for about 40 hours. After completion of the reaction, the reaction mixture was cooled to room temperature, and then filtered. A solid phase of the reaction mixture was discarded and the filtrate was concentrated under vacuum. MC (200 ml) and purified water (300 ml) are added to the concentrate and stirred for 30 min, and then an organic layer is separated. The organic layer was treated with MgSO₄, concentrated under vacuum, and then subjected to column purification with MC-methanol. 15.7 g of tetraethyl 2,2',2",2'''-(1,4,7,10-tetraazacyclododecane-1,4,7,10-tetrayl)tetraacetate was obtained (Yield: 52.3%).

$^1$H NMR (CDCl₃): 4.19 (q, 8H), 3.19 (s, 8H), 2.48 (s, 16H), 1.27 (t, 12H)

Tetraethyl 2,2',2",2'''-(1,4,7,10-tetraazacyclododecane-1,4,7,10-tetrayl)tetraacetate (15.7 g), NaOH (5.6 g), methanol (95 ml) and purified water (60 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (200 ml). The extracted organic layer was treated with MgSO₄. 9.9 g of the title compound was obtained (Yield: 80.5%).

$^1$H NMR (DMSO): 3.88 (s, 8H), 3.23 (s, 16H)

Embodiment 6

Preparation of 4,4',4",4'''-(1,4,7,10-tetraazacyclododecane-1,4,7,10-tetrayl)tetrabenzoic acid (Formula (2f))

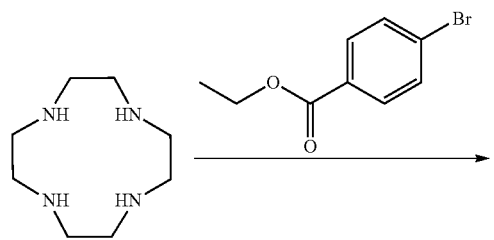

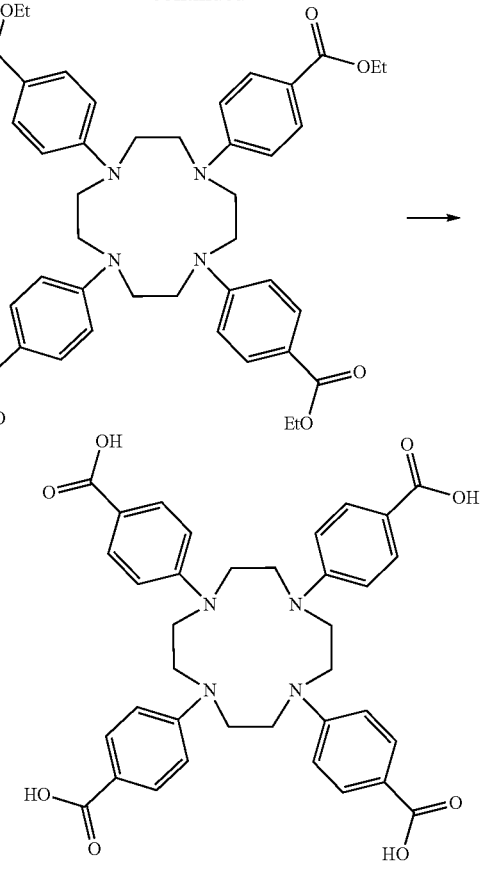

(2f)

Cyclen (10.0 g), ethyl 4-bromobenzoate (58.5 g), t-BuONa (27.9 g) and toluene (400 ml) were added, stirred, and then heated to 35° C. 50% (t-Bu)₃P toluene solution (2.4 g) was added, stirred for about 30 min and then heated to 50° C. Pd(dba)₂ (1.7 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO₄, concentrated under vacuum, and then subjected to column purification with MC-methanol. 15.8 g of tetraethyl 4,4',4",4'''-(1,4,7,10-tetraazacyclododecane-1,4,7,10-tetrayl)tetrabenzoate was obtained (Yield: 35.6%)

$^1$H NMR (CDCl₃): 7.81 (d, 8H), 6.98 (d, 8H), 4.15 (q, 8H), 3.48 (s, 16H), 1.25 (t, 12H)

Tetraethyl 4,4',4",4'''-(1,4,7,10-tetraazacyclododecane-1,4,7,10-tetrayl)tetrabenzoate (15.8 g), NaOH (3.8 g), methanol (130 ml) and purified water (100 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (130 ml). The extracted organic layer was treated with MgSO₄. 11.5 g of the title compound was obtained (Yield: 85.2%).

$^1$H NMR (DMSO): 7.82 (d, 8H), 6.97 (d, 8H), 3.45 (s, 16H)

Embodiment 7

Preparation of 5,5',5'',5'''-(1,4,7,10-tetraazacyclodo-decane-1,4,7,10-tetrayl)tetranicotinic acid (Formula (2g))

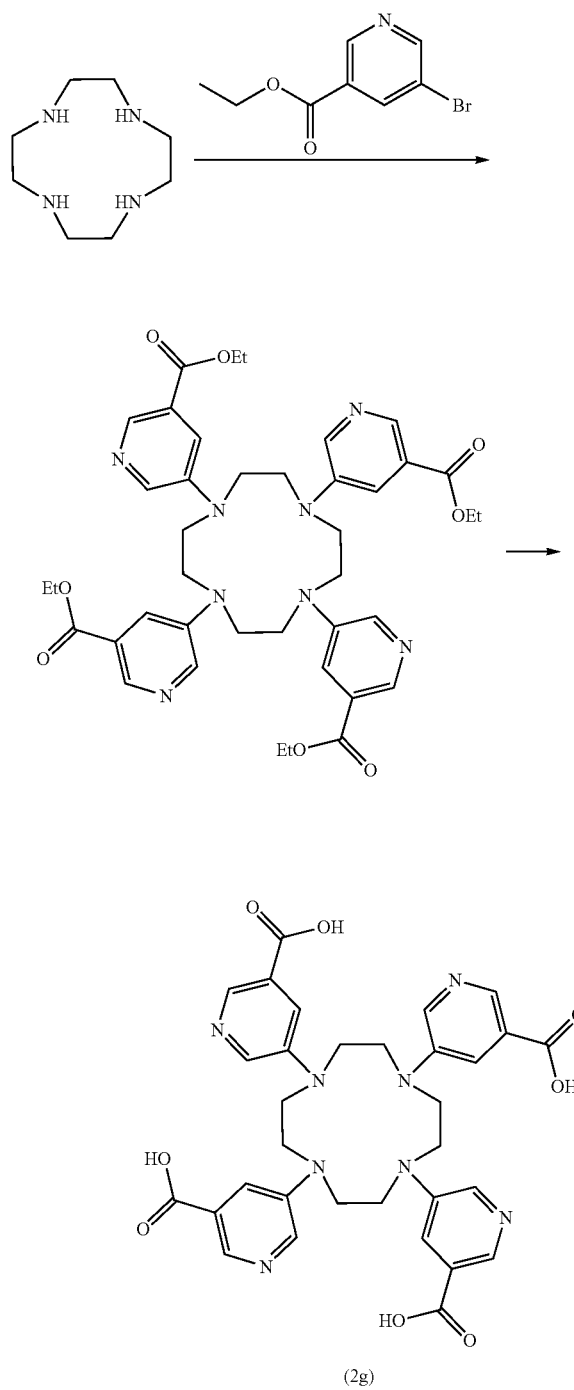

Cyclen (10.0 g), 5-bromonicotinate (58.7 g), t-BuONa (27.9 g) and xylene (400 ml) were added, stirred, and then heated to 35° C. 50% (t-Bu)$_3$P toluene solution (2.4 g) was added, stirred for about 30 min and then heated to 50° C. Pd(dba)$_2$ (1.7 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO$_4$, concentrated under vacuum, and then subjected to column purification with MC-methanol. 17.9 g of tetraethyl 5,5',5'',5'''-(1,4,7,10-tetraazacyclododecane-1,4,7,10-tetrayl)tetranicotinate was obtained (Yield: 40.1%)

$^1$H NMR (CDCl$_3$): 8.95 (d, 4H), 8.46 (d, 4H), 7.83 (d, 4H), 4.21 (q, 8H), 3.38 (s, 16H), 1.24 (t, 12H)

Tetraethyl 5,5',5'',5'''-(1,4,7,10-tetraazacyclododecane-1,4,7,10-tetrayl)tetranicotinate (17.9 g), NaOH (4.3 g), methanol (150 ml) and purified water (110 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (160 ml). The extracted organic layer was treated with MgSO$_4$. 11.6 g of the title compound was obtained (Yield: 75.6%).

$^1$H NMR (DMSO): 8.96 (d, 4H), 8.44 (d, 4H), 7.84 (d, 4H), 3.36 (s, 16H)

Embodiment 8

Preparation of 5,5',5'',5'''-(1,4,7,10-tetraazacyclododecane-1,4,7,10-tetrayl)tetrakis(furan-2-carboxylic acid) (Formula (2h))

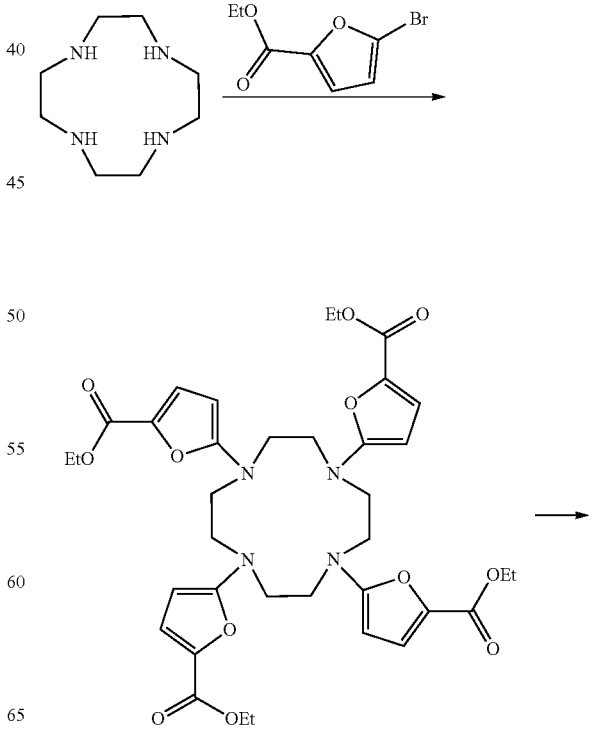

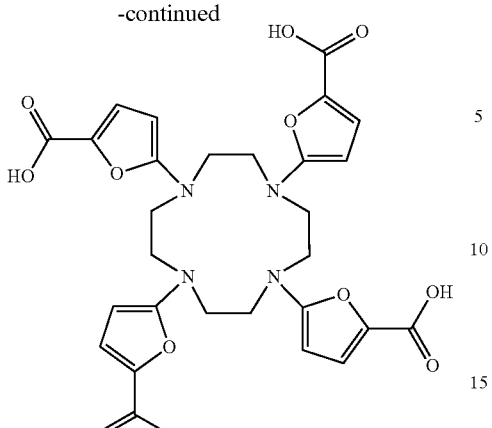

(2h)

Cyclen (10.0 g), ethyl 5-bromofuran-2-carboxylate (56.0 g), t-BuONa (27.9 g) and toluene (400 ml) were added, stirred, and then heated to 35° C. 50% (t-Bu)₃P toluene solution (2.4 g) was added, stirred for about 30 min and then heated to 50° C. Pd(dba)₂ (1.7 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO₄, concentrated under vacuum, and then subjected to column purification with MC-methanol. 12.6 g of tetraethyl 5,5',5",5"'-(1,4,7,10-tetraazacyclododecane-1,4,7,10-tetrayl)tetrakis(furan-2-carboxylat e) was obtained (Yield: 30.0%)

$^1$H NMR (CDCl₃): 7.39 (d, 8H), 4.35 (q, 8H), 3.28 (s, 16H), 1.35 (t, 12H)

Tetraethyl 5,5',5",5"'-(1,4,7,10-tetraazacyclododecane-1,4,7,10-tetrayl)tetrakis(furan-2-carboxylat e) (12.6 g), NaOH (3.2 g), methanol (100 ml) and purified water (75 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (100 ml). The extracted organic layer was treated with MgSO₄. 7.9 g of the title compound was obtained (Yield: 73.9%).

$^1$H NMR (DMSO): 7.40 (d, 8H), 3.29 (s, 16H)

Synthesis of Cyclam Derivative

Embodiment 9

Preparation of 2,2',2",2"'-(1,4,8,11-tetraazacyclotetradecane-1,4,8,11-tetrayl)tetraacetic acid (Formula (3e))

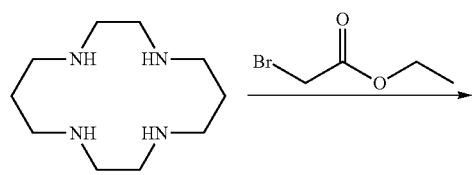

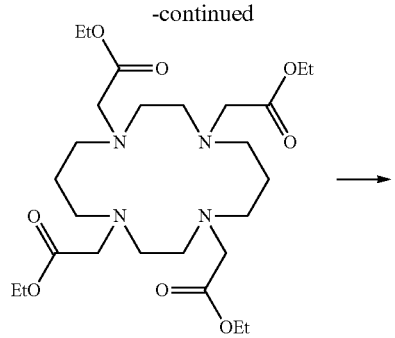

(3e)

Cyclam (10.0 g) was dissolved in acetonitrile (400 ml). K₂CO₃ (34.5 g) and ethyl bromoacetate (36.7 g) were added and reaction mixture was heated under stirring and under reflux for about 40 hours. After completion of the reaction, the reaction mixture was cooled to room temperature, and then filtered. A solid phase of the reaction mixture was discarded and the filtrate was concentrated under vacuum. MC (200 ml) and purified water (300 ml) are added to the concentrate and stirred for 30 min, and then an organic layer is separated. The organic layer was treated with MgSO₄, concentrated under vacuum, and then subjected to column purification with MC-methanol. 15.4 g of tetraethyl 2,2',2",2"'-(1,4,8,11-tetraazacyclotetradecane-1,4,8,11-tetrayl)tetraacetate was obtained (Yield: 56.8%).

$^1$H NMR (CDCl₃): 4.12 (q, 8H), 3.36 (s, 8H), 2.69~2.73 (m, 16H), 1.60 (m, 4H), 1.26 (t, 12H)

Tetraethyl 2,2',2",2"'-(1,4,8,11-tetraazacyclotetradecane-1,4,8,11-tetrayl)tetraacetate (15.4 g), NaOH (5.2 g), methanol (90 ml) and purified water (60 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (200 ml). The extracted organic layer was treated with MgSO₄. 9.3 g of the title compound was obtained (Yield: 75.9%).

$^1$H NMR (D₂O): 3.51 (s, 8H), 3.14 (s, 8H), 3.07 (t, 8H), 1.85 (q, 4H)

Embodiment 10

Preparation of 4,4',4'',4'''-(1,4,8,11-tetraazacyclotetradecane-1,4,8,11-tetrayl)tetrabenzoic acid (Formula (30))

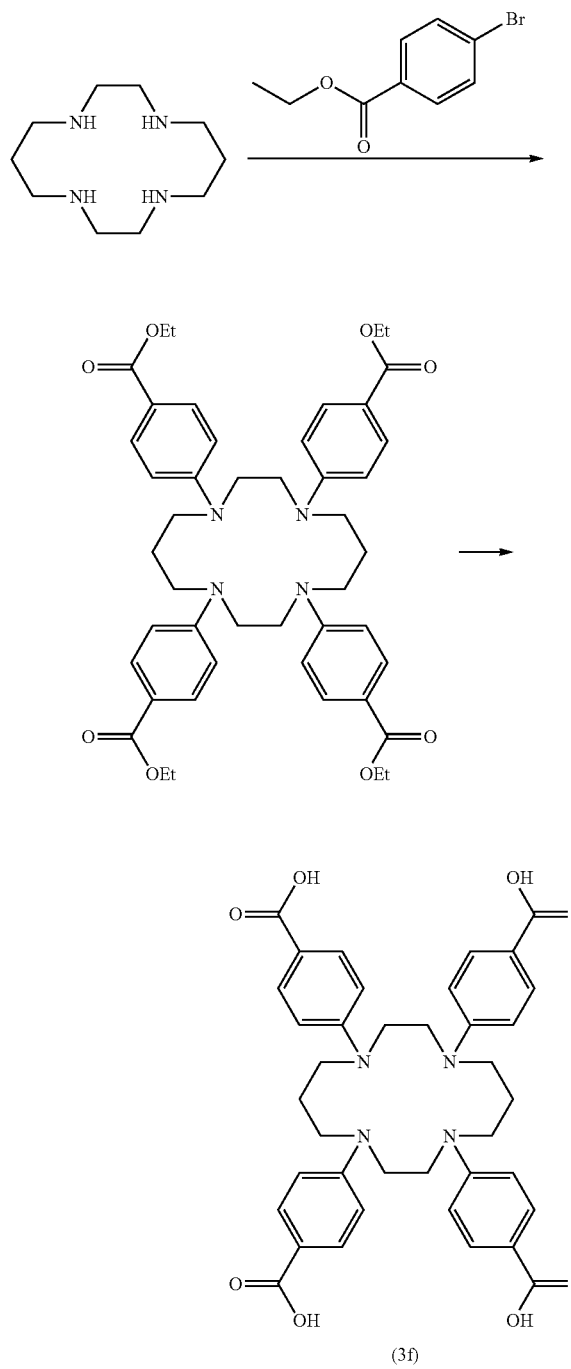

(3f)

Cyclam (10.0 g), ethyl 4-bromobenzoate (50.3 g), t-BuONa (24.0 g) and toluene (400 ml) were added, stirred, and then heated to 35° C. 50% (t-Bu)$_3$P toluene solution (2.0 g) was added, stirred for about 30 min and then heated to 50° C. Pd(dba)$_2$ (1.5 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO$_4$, concentrated under vacuum, and then subjected to column purification with MC-methanol. 12.3 g of tetraethyl 4,4',4'',4'''-(1,4,8,11-tetraazacyclotetradecane-1,4,8,11-tetrayl)tetrabenzoate was obtained (Yield: 31.0%)

$^1$H NMR (CDCl$_3$): 7.80 (d, 8H), 6.94 (d, 8H), 4.13 (q, 8H), 2.65~2.71 (m, 16H), 1.65 (m, 4H), 1.26 (t, 12H)

Tetraethyl 4,4',4'',4'''-(1,4,8,11-tetraazacyclotetradecane-1,4,8,11-tetrayl)tetrabenzoate (12.3 g), NaOH (2.6 g), methanol (70 ml) and purified water (100 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (100 ml). The extracted organic layer was treated with MgSO$_4$. 8.6 g of the title compound was obtained (Yield: 81.2%).

$^1$H NMR (DMSO): 7.83 (d, 8H), 6.95 (d, 8H), 2.63~2.73 (m, 16H), 1.62 (m, 4H)

Embodiment 11

Preparation of 5,5',5'',5'''-(1,4,8,11-tetraazacyclotetradecane-1,4,8,11-tetrayl)tetranicotinic acid (Formula (3g))

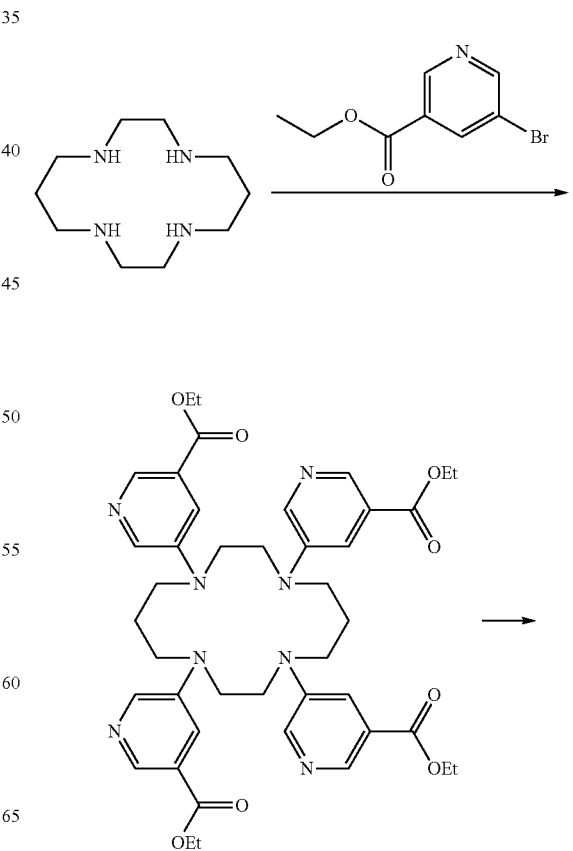

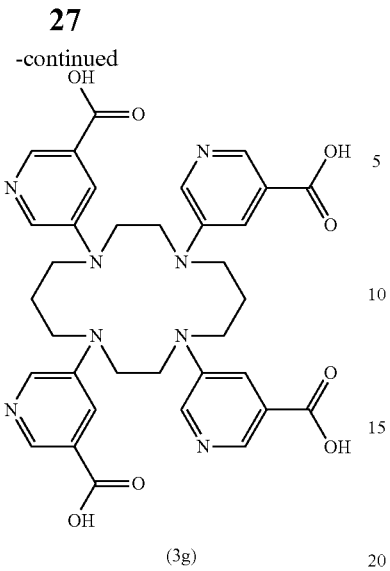

(3g)

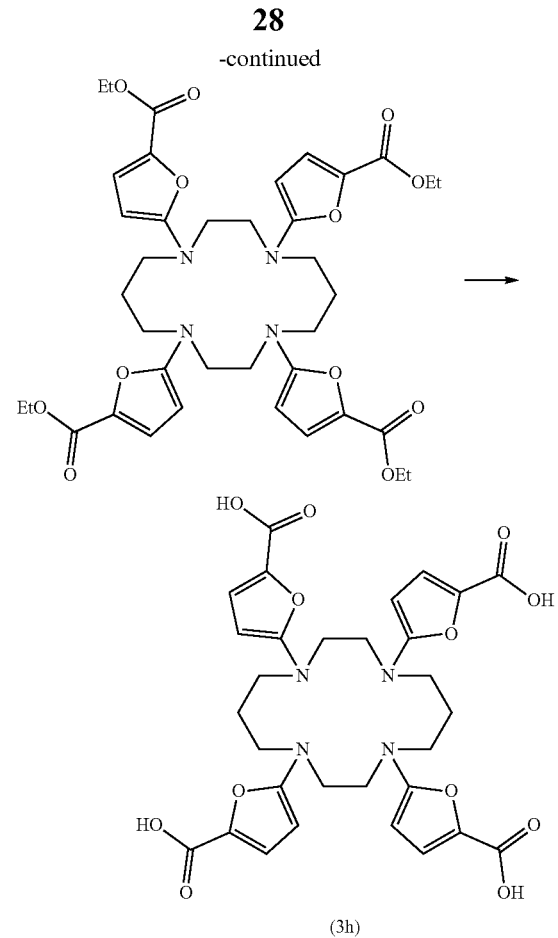

(3h)

Cyclam (10.0 g), ethyl 5-bromonicotinate (50.3 g), t-BuONa (24.0 g) and xylene (400 ml) were added, stirred, and then heated to 35° C. 50% (t-Bu)₃P toluene solution (2.0 g) was added, stirred for about 30 min and then heated to 50° C. Pd(dba)₂ (1.5 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO₄, concentrated under vacuum, and then subjected to column purification with MC-methanol. 11.1 g of tetraethyl 5,5',5",5'''-(1,4,8,11-tetraazacyclotetradecane-1,4,8,11-tetrayl)tetranicotinate was obtained (Yield: 27.8%)

¹H NMR (CDCl₃): 8.91 (d, 4H), 8.37 (d, 4H), 7.85 (d, 4H), 4.15 (q, 8H), 2.67~2.64 (m, 16H), 1.71 (m, 4H), 1.24 (t, 12H)

Tetraethyl 5,5',5",5'''-(1,4,8,11-tetraazacyclotetradecane-1,4,8,11-tetrayl)tetranicotinate (11.1 g), NaOH (2.6 g), methanol (90 ml) and purified water (70 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (120 ml). The extracted organic layer was treated with MgSO₄. 7.4 g of the title compound was obtained (Yield: 77.6%).

¹H NMR (DMSO): 8.93 (d, 4H), 8.38 (d, 4H), 7.85 (d, 4H), 2.67~2.66 (m, 16H), 1.72 (m, 4H)

Embodiment 12

Preparation of 5,5',5",5'''-(1,4,8,11-tetraazacyclotetradecane-1,4,8,11-tetrayl)tetrakis(furan-2-carboxylic acid) (Formula (3h))

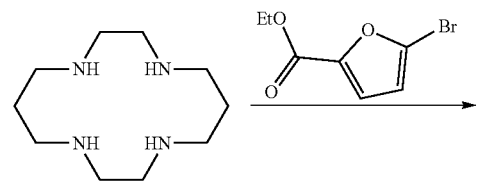

Cyclam (10.0 g), ethyl 5-bromofuran-2-carboxylate (48.1 g), t-BuONa (24.0 g) and toluene (400 ml) were added, stirred, and then heated to 35° C. 50% (t-Bu)₃P toluene solution (2.0 g) was added, stirred for about 30 min and then heated to 50° C. Pd(dba)₂ (1.5 g) was added, heated under reflux. After completion of the reaction, the reaction mixture was cooled to room temperature. a purified water (1000 ml) was added, stirred for 30 min, and then an organic layer is separated. An aqueous layer of the reaction mixture was discarded. The organic layer was treated with MgSO₄, concentrated under vacuum, and then subjected to column purification with MC-methanol. 14.1 g of tetraethyl 5,5',5",5'''-(1,4,8,11-tetraazacyclotetradecane-1,4,8,11-tetrayl)tetrakis(furan-2-carboxylate) was obtained (Yield: 37.5%)

¹H NMR (CDCl₃): 7.40 (d, 8H), 4.23 (q, 8H), 2.65~2.71 (m, 16H), 1.66 (m, 4H), 1.29 (t, 12H)

Tetraethyl 5,5',5",5'''-(1,4,8,11-tetraazacyclotetradecane-1,4,8,11-tetrayl)tetrakis(furan-2-carboxylate) (14.1 g), NaOH (3.5 g), methanol (110 ml) and purified water (85 ml) were added and the reaction mixture was heated to 55-60° C., stirred for 12 hours. After completion of the reaction, the reaction mixture was cooled to about 40° C. and concentrated under vacuum. The solvent was removed. The reaction mixture was adjusted to pH 5-6 with 10% aqueous HCl, stirred for 30 min, and extracted with MC (120 ml). The extracted organic layer was treated with MgSO₄. 9.4 g of the title compound was obtained (Yield: 78.1%).

¹H NMR (DMSO): 7.41 (d, 8H), 2.69~2.72 (m, 16H), 1.68 (m, 4H)

Experimental Example 1: Removal Test of Heavy Metals of Active Ingredients (1) Preparation of Heavy Metal Contamination Sources and Pig Skin Samples 162.1 mg of Pb(NO$_3$)$_2$, 211.2 mg of Cd(NO$_3$)$_2$ and 292.3 mg of Zn(NO$_3$)$_2$ were added to 1 L of distilled water to prepare a 100 ppm aqueous solution of heavy metal contamination sources respectively.

Trientine, cyclen, cyclam, the derivatives thereof prepared by Embodiments 1 to 12 and EDTA as Comparative Example 1, were added to 100 ml of distilled water to prepare 0.1 wt %, 0.5 wt %, and 1.0 wt % of active ingredient samples respectively.

A pig was slaughtered, flayed and the bristle was shaved. The pig skin was cut to prepare 5*5 cm size of skin samples respectively.

(2) Test 1.0 ml of heavy metal contamination sources were treated to pig skin samples respectively and skin samples were left at room temperature for 10 min for heavy metal to be attached or absorbed on skin samples, and then, the said active ingredients samples were treated to the contaminated skin samples and the skin samples were left for 2 min. The said skin samples were cleanly wiped with wet gauze, and then, added to 50 ml of methanol and extracted by shaking with ultrasonic for 60 min. 50 ml of methanol was further added and mixed. The pig skin samples were removed from the extracted solutions to prepare the test solutions.

The test solutions were analyzed for heavy metal components using an inductively coupled plasma mass spectrometer (ICP-MS, Xseries™ 2, Thermo Fisher Scientific, UK).

In ICP-MS, the specific mass-to-charge ratio (m/z) of lead (Pb) is 206-208, that of cadmium (Cd) is 114, and that of zinc (Zn) is 66-68. The heavy metal removal rate was calculated according to the following Equation 1, and the test result is shown in Table 1 and FIG. 1 to FIG. 3.

$$\text{Removing rate}(\%) = \left(1 - \frac{\text{Heavy metal balance of pig skin}}{\text{Amount of heavy metal treatment}}\right) \times 100 \quad \text{Equation 1}$$

TABLE 1

| Samples | | Removal of Heavy metals | | |
|---|---|---|---|---|
| Active ingredient | Content (wt %) | Pb (%) | Cd (%) | Cu (%) |
| Trientine | 0.1% | 89.7 | 87.3 | 92.6 |
| | 0.5% | 92.1 | 92.4 | 95.4 |
| | 1.0% | 92.3 | 92.3 | 96.0 |
| Embodiment 1 | 0.1% | 91.1 | 91.0 | 95.2 |
| | 0.5% | 92.0 | 93.0 | 97.3 |
| | 1.0% | 92.1 | 94.1 | 97.5 |
| Embodiment 2 | 0.1% | 86.4 | 87.3 | 93.5 |
| | 0.5% | 88.6 | 89.7 | 95.8 |
| | 1.0% | 89.0 | 90.5 | 96.9 |
| Embodiment 3 | 0.1% | 87.2 | 87.1 | 91.4 |
| | 0.5% | 89.4 | 90.2 | 94.9 |
| | 1.0% | 90.9 | 90.8 | 95.3 |
| Embodiment 4 | 0.1% | 86.2 | 87.7 | 92.5 |
| | 0.5% | 89.7 | 90.6 | 96.2 |
| | 1.0% | 90.8 | 91.8 | 97.2 |
| Cyclen | 0.1% | 91.7 | 88.6 | 93.1 |
| | 0.5% | 93.7 | 91.1 | 96.6 |
| | 1.0% | 94.3 | 91.4 | 97.8 |
| Embodiment 5 | 0.1% | 92.4 | 90.4 | 94.6 |
| | 0.5% | 94.7 | 93.6 | 96.8 |
| | 1.0% | 95.1 | 93.7 | 97.2 |
| Embodiment 6 | 0.1% | 90.2 | 89.2 | 94.1 |
| | 0.5% | 92.8 | 90.9 | 96.3 |
| | 1.0% | 93.2 | 91.6 | 97.0 |
| Embodiment 7 | 0.1% | 90.8 | 87.9 | 93.8 |
| | 0.5% | 93.1 | 89.4 | 95.1 |
| | 1.0% | 93.6 | 90.7 | 96.0 |
| Embodiment 8 | 0.1% | 91.4 | 90.4 | 94.3 |
| | 0.5% | 93.4 | 91.3 | 96.8 |
| | 1.0% | 94.0 | 93.4 | 97.2 |
| Cyclam | 0.1% | 86.9 | 87.3 | 94.0 |
| | 0.5% | 88.6 | 89.5 | 97.1 |
| | 1.0% | 90.1 | 91.4 | 97.8 |
| Embodiment 9 | 0.1% | 88.9 | 89.1 | 94.3 |
| | 0.5% | 91.0 | 91.3 | 96.9 |
| | 1.0% | 91.4 | 91.9 | 97.3 |
| Embodiment 10 | 0.1% | 88.3 | 85.7 | 94.1 |
| | 0.5% | 90.5 | 90.4 | 96.0 |
| | 1.0% | 90.9 | 91.1 | 96.5 |
| Embodiment 11 | 0.1% | 87.9 | 86.7 | 93.8 |
| | 0.5% | 89.2 | 88.9 | 96.0 |
| | 1.0% | 91.2 | 91.0 | 96.8 |
| Embodiment 12 | 0.1% | 89.1 | 90.1 | 94.5 |
| | 0.5% | 90.9 | 90.7 | 95.8 |
| | 1.0% | 91.3 | 90.9 | 96.3 |
| Comparative Example 1(EDTA) | 0.1% | 84.3 | 82.3 | 86.5 |
| | 0.5% | 88.3 | 87.3 | 88.6 |
| | 1.0% | 89.6 | 88.3 | 89.2 |
| Control 1 | — | 74.6 | 76.2 | 76.8 |

As shown in Table 1 and FIG. 1 to FIG. 3, 0.1 wt % of the heavy metal chelating compounds according to the present invention have 89.2% of Pb removal rate, 88.4% of average removal rate of Cd, 93.7% of Cu removal rate. These compounds of the present invention have the remarkably removal ability of heavy metals attached or absorbed on the skin in comparison with the EDTA of Comparative Example 1 (Pb 84.3%, Cd 82.3%, Cu 86.5%) and Control 1 without the chelate (Pb 74.6%, Cd 76.2%, Cu 76.8%).

The same results are obtained even in 0.5 wt % and 1.0 wt % of the aqueous solution. However, the difference of heavy metal removal rate between 0.5 wt % and 1.0 wt % of the said examples is not remarkable. This means that heavy metals can be sufficiently removed at 0.5 wt % of the aqueous solution.

Experimental Example 2: Skin Irritation Test of Active Ingredient

A total of 20 people (10 men and 10 women in their 20 s and 30 s) were tested for skin irritation using the patch method according to the guidelines of CTFA (The Cosmetic, Toiletry & Fragrance Association, Inc. Washington, D.C.).

A filter paper disk was placed in an 8 mm diameter, 10 panels of pin chamber. Then, 20 µl each of the compositions according to Experimental Example 1 was dropped on a filter paper disk, naturally dried for 10 min, and then the pin chambers were attached to the subject's back region with a Scanpor tape.

After 24 hours, the pin chamber was removed, and skin conditions were visually observed. The degree and grade for skin irritation were calculated according to the following Equation 2, and the results are shown in Table 2 below.

$$\text{Degree of irritation} = \left[ \frac{(\pm)\text{No.} \times 1 + (+)\text{No.} \times 2 + (++)\text{No.} \times 3}{\text{Total number of subject}} \right] \quad \text{Equation 2}$$

[Criteria for Skin Irritation]

(−): No erythema or particularly no symptoms; (±): slightly reddish than the periphery; (+): Apparent reddening than periphery; (++): More reddened and swollen than periphery.

[Grade for Skin Irritation]

Degree of irritation 0-0.1: Grade I (unstimulated);

Degree of irritation 0.11-0.3: Grade II (weakly stimulated);

Degree of irritation 0.31-0.5: Grade III (moderately stimulated);

Degree of irritation 0.51 or more: Grade IV (strongly stimulated)

TABLE 2

| Active ingredient | Content (Wt %) | Samples Test result (number of subject) (−) | (±) | (+) | (++) | Degree of irritation | Grade |
|---|---|---|---|---|---|---|---|
| Trientine | 0.1% | 20 | 0 | 0 | 0 | 0 | I |
|  | 0.5% | 19 | 1 | 0 | 0 | 0.05 | I |
|  | 1.0% | 17 | 3 | 0 | 0 | 0.15 | II |
| Embodiment 1 | 0.1% | 20 | 0 | 0 | 0 | 0 | I |
|  | 0.5% | 19 | 1 | 0 | 0 | 0.05 | I |
|  | 1.0% | 16 | 4 | 0 | 0 | 0.20 | II |
| Embodiment 2 | 0.1% | 20 | 0 | 0 | 0 | 0 | I |
|  | 0.5% | 20 | 0 | 0 | 0 | 0 | I |
|  | 1.0% | 19 | 1 | 0 | 0 | 0.05 | I |
| Embodiment 3 | 0.1% | 20 | 0 | 0 | 0 | 0 | I |
|  | 0.5% | 20 | 0 | 0 | 0 | 0 | I |
|  | 1.0% | 19 | 1 | 0 | 0 | 0.05 | I |
| Embodiment 4 | 0.1% | 20 | 0 | 0 | 0 | 0 | I |
|  | 0.5% | 20 | 0 | 0 | 0 | 0 | I |
|  | 1.0% | 19 | 1 | 0 | 0 | 0.05 | I |
| Cyclen | 0.1% | 20 | 0 | 0 | 0 | 0 | I |
|  | 0.5% | 20 | 0 | 0 | 0 | 0 | I |
|  | 1.0% | 18 | 1 | 1 | 0 | 0.15 | II |
| Embodiment 5 | 0.1% | 20 | 0 | 0 | 0 | 0 | I |
|  | 0.5% | 20 | 0 | 0 | 0 | 0 | I |
|  | 1.0% | 19 | 1 | 0 | 0 | 0.05 | I |
| Embodiment 6 | 0.1% | 20 | 0 | 0 | 0 | 0 | I |
|  | 0.5% | 20 | 0 | 0 | 0 | 0 | I |
|  | 1.0% | 19 | 1 | 0 | 0 | 0.05 | I |
| Embodiment 7 | 0.1% | 20 | 0 | 0 | 0 | 0 | I |
|  | 0.5% | 20 | 0 | 0 | 0 | 0 | I |
|  | 1.0% | 20 | 0 | 0 | 0 | 0 | I |
| Embodiment 8 | 0.1% | 20 | 0 | 0 | 0 | 0 | I |
|  | 0.5% | 20 | 0 | 0 | 0 | 0 | I |
|  | 1.0% | 18 | 2 | 0 | 0 | 0.10 | I |
| Cyclam | 0.1% | 20 | 0 | 0 | 0 | 0 | I |
|  | 0.5% | 19 | 1 | 0 | 0 | 0.05 | I |
|  | 1.0% | 17 | 3 | 0 | 0 | 0.15 | II |
| Embodiment 9 | 0.1% | 20 | 0 | 0 | 0 | 0 | I |
|  | 0.5% | 20 | 0 | 0 | 0 | 0 | I |
|  | 1.0% | 18 | 2 | 0 | 0 | 0.10 | I |
| Embodiment 10 | 0.1% | 20 | 0 | 0 | 0 | 0 | I |
|  | 0.5% | 20 | 0 | 0 | 0 | 0 | I |
|  | 1.0% | 19 | 1 | 0 | 0 | 0.05 | I |
| Embodiment 11 | 0.1% | 20 | 0 | 0 | 0 | 0 | I |
|  | 0.5% | 20 | 0 | 0 | 0 | 0 | I |
|  | 1.0% | 18 | 2 | 0 | 0 | 0.10 | I |
| Embodiment 12 | 0.1% | 20 | 0 | 0 | 0 | 0 | I |
|  | 0.5% | 20 | 0 | 0 | 0 | 0 | I |
|  | 1.0% | 19 | 1 | 0 | 0 | 0.05 | I |
| Comparative Example 1 (EDTA) | 0.1% | 20 | 2 | 0 | 0 | 0.10 | I |
|  | 0.5% | 17 | 2 | 1 | 0 | 0.20 | II |
|  | 1.0% | 15 | 3 | 2 | 0 | 0.35 | III |

As shown in Table 2, all of the compounds according to the present invention have grade I, which is a non-stimulating range, within the concentration range of 0.5 wt % in the human skin irritation test. In the concentration range of 1.0 wt %, trientine, cyclen and cyclam have grade II (light stimulus range), whereas all of these aromatic and heterocyclic derivatives have grade I, indicating that skin irritation reduction is improved. On the other hand, The EDTA of Comparative Example 1 was evaluated to be grade III (moderate irritation range) at a concentration of 1.0 wt %, indicating that the skin irritation is higher than those of the compounds of the present invention.

Experimental Example 3: Formaldehyde Removing Ability Test

Purified water was added to 35.0% formaldehyde solution to prepare a 2.0% diluted solution of formaldehyde. 3 molar equivalents of Trientine, cyclen, cyclam, and derivative compounds of the present invention were added to the diluted solution, and the change of amount of formaldehyde was analyzed by gas chromatography (GC) while stirring at room temperature.

The content of formaldehyde was measured under the following analysis conditions in the initial state, after 30 min and 180 min, the result was shown in Table 3.

<GC Analysis Conditions>

Detector: Flame ionization detector

Column: ZB-1 (0.32 mm×30 m, 3.00 m) or a similar column.

Headspace conditions: equilibrium temperature 60° C., equilibration time 10 min, transfer line temperature 65° C.

Column temperature: Keep at 50° C. for the first 5 min, then increase the temperature to 200° C. by 30° C. per minute and maintain at 200° C. for 10 min.

Sample inlet temperature: constant temperature around 140° C.

Detector temperature: constant temperature around 250° C.

Carrier gas: nitrogen

Split ratio: about 1:20

Flow rate: 2.5 mL/min

Injection amount: 5 μL of the sample solution is injected into the vial with microsyringe. 1 mL of the vapor phase is injected into the column according to the head space conditions.

Analysis time: 20 min

TABLE 3

| Active ingredient | Area (mAU*min) | | |
|---|---|---|---|
| | Initial | 30 min | 180 min |
| Trientine | 0.305 | 0.168 | 0 |
| Embodiment 1 | 0.305 | 0.170 | 0 |
| Embodiment 2 | 0.305 | 0.168 | 0 |
| Embodiment 3 | 0.305 | 0.171 | 0 |
| Embodiment 4 | 0.305 | 0.173 | 0 |
| Cyclen | 0.305 | 0.181 | 0 |
| Embodiment 5 | 0.305 | 0.179 | 0 |
| Embodiment 6 | 0.305 | 0.183 | 0 |
| Embodiment 7 | 0.305 | 0.181 | 0 |
| Embodiment 8 | 0.305 | 0.168 | 0 |
| Cyclam | 0.305 | 0.172 | 0 |
| Embodiment 9 | 0.305 | 0.182 | 0 |
| Embodiment 10 | 0.305 | 0.171 | 0 |
| Embodiment 11 | 0.305 | 0.174 | 0 |
| Embodiment 12 | 0.305 | 0.170 | 0 |

As shown in Table 3, GC analysis shows that the formaldehyde was remarkably reduced by about 40% to 45% in 30 min after the addition of the compounds of the present invention and completely undetected after 180 min. This means that the compounds of the present invention effectively remove formaldehyde.

Embodiments 13 to 27: Preparation of Composition for Protecting Skin

Compositions which comprise 5 wt % trientine, cyclen, cyclam and the trientine derivatives, cyclen derivatives and cyclam derivatives prepared in the Embodiments 1 to 12 were prepared in the formulation of an oil-in-water (O/W) emulsion.

The ingredients of the composition are shown in Table 4 below.

TABLE 4

| Composition | Active ingredient | Content of active ingredient(wt %) | Cosmetic ingredients (wt %) |
|---|---|---|---|
| Embodiment 13 | Trientine | 0.5 | Purified water (up to 100%) Glycerin (6.0%) Butylene glycol (5.0%) Sodium hyaruronate (4.0%) Cetostearyl alcohol (1.0%) Stearic acid (2.0%) PEG-100 stearate (1.0%) Squalane (4.0%) Polysorbate 60 (2.0%) antiseptic (little bit) perfume (little bit) |
| Embodiment 14 | Embodiment 1 | 0.5 | |
| Embodiment 15 | Embodiment 2 | 0.5 | |
| Embodiment 16 | Embodiment 3 | 0.5 | |
| Embodiment 17 | Embodiment 4 | 0.5 | |
| Embodiment 18 | Cyclen | 0.5 | |
| Embodiment 19 | Embodiment 5 | 0.5 | |
| Embodiment 20 | Embodiment 6 | 0.5 | |
| Embodiment 21 | Embodiment 7 | 0.5 | |
| Embodiment 22 | Embodiment 8 | 0.5 | |
| Embodiment 23 | Cyclam | 0.5 | |
| Embodiment 24 | Embodiment 9 | 0.5 | |
| Embodiment 25 | Embodiment 10 | 0.5 | |
| Embodiment 26 | Embodiment 11 | 0.5 | |
| Embodiment 27 | Embodiment 12 | 0.5 | |
| Comparative Example 2 | EDTA | 0.5 | |
| Control 2 | — | — | |

The compositions for skin were prepared in the following steps.

(1) The active ingredient was added to purified water, mixed to dissolve.

(2) Glycerin, butylene glycol, sodium hyaruronate and cetostearyl alcohol were added to the said purified water, and the mixture was heated to 70° C. and dissolved to prepare an aqueous solution.

(3) Stearic acid, PEG-100 stearate, squalane, polysorbate 60, preservative and perfume were mixed and heated to 70° C. to prepare an oily solution.

(4) The oily solution was gradually added to the aqueous solution while stirring, to prepare a composition for the skin of the oil-in-water emulsion formulation.

Experimental Example 4: Heavy Metals Removal Ability of Compositions for Skin

The compositions for skin prepared according to Embodiments 13 to 27, Comparative Example 2 and Control 2 were tested for the heavy metal removal ability.

The tests were carried out in the same manner as in Experimental Example 1, and the results are shown in Table 5 below.

TABLE 5

| Samples | | Removal of Heavy metals | | |
| --- | --- | --- | --- | --- |
| Composition | Active ingredient | Pb (%) | Cd (%) | Cu (%) |
| Embodiment 13 | Trientine | 92.5 | 93.2 | 95.9 |
| Embodiment 14 | Embodiment 1 | 92.4 | 93.4 | 97.7 |
| Embodiment 15 | Embodiment 2 | 89.6 | 91.1 | 96.1 |
| Embodiment 16 | Embodiment 3 | 89.6 | 90.8 | 95.2 |
| Embodiment 17 | Embodiment 4 | 90.1 | 91.2 | 96.4 |
| Embodiment 18 | Cyclen | 93.6 | 91.3 | 96.9 |
| Embodiment 19 | Embodiment 5 | 94.9 | 93.9 | 96.8 |
| Embodiment 20 | Embodiment 6 | 93.4 | 91.2 | 96.1 |
| Embodiment 21 | Embodiment 7 | 93.7 | 90.1 | 95.3 |
| Embodiment 22 | Embodiment 8 | 93.5 | 91.6 | 96.7 |
| Embodiment 23 | Cyclam | 90.2 | 89.9 | 97.6 |
| Embodiment 24 | Embodiment 9 | 91.0 | 91.5 | 97.2 |
| Embodiment 25 | Embodiment 10 | 91.2 | 90.9 | 96.6 |
| Embodiment 26 | Embodiment 11 | 89.7 | 89.3 | 96.4 |
| Embodiment 27 | Embodiment 12 | 91.4 | 90.6 | 96.0 |
| Comparative Example 2 | EDTA | 88.6 | 87.5 | 89.1 |
| Control 2 | — | 76.8 | 77.5 | 78.1 |

As shown in Table 5 and FIG. 4, 0.5 wt % of the heavy metal chelating compositions according to Embodiments 13 to 27 have 91.8% of Pb removal rate, 91.3% of average removal rate of Cd, 96.5% of Cu removal rate. These compounds of the present invention have the remarkably removal ability of heavy metals attached or absorbed on the skin in comparison with the EDTA of Comparative Example 2 (Pb 88.6%, Cd 87.5%, Cu 89.1%) and Control 2 without the chelate (Pb 76.8%, Cd 77.5%, Cu 78.1%), Experimental Example 5: Skin Irritation Test of Compositions for Skin The compositions for skin prepared according to Embodiments 13 to 27, Comparative Example 2 were tested for the skin irritation.

The tests were carried out in the same manner as in Experimental Example 2, and the results are shown in Table 6 below.

TABLE 6

| Samples | | Test result(number of subject) | | | | Degree of irritation | Grade |
| --- | --- | --- | --- | --- | --- | --- | --- |
| Composition | Active ingredient | (−) | (±) | (+) | (++) | | |
| Embodiment 13 | Trientine | 19 | 1 | 0 | 0 | 0.05 | I |
| Embodiment 14 | Embodiment 1 | 19 | 1 | 0 | 0 | 0.05 | I |
| Embodiment 15 | Embodiment 2 | 20 | 0 | 0 | 0 | 0 | I |
| Embodiment 16 | Embodiment 3 | 20 | 0 | 0 | 0 | 0 | I |
| Embodiment 17 | Embodiment 4 | 20 | 0 | 0 | 0 | 0 | I |
| Embodiment 18 | Cyclen | 20 | 0 | 0 | 0 | 0 | I |
| Embodiment 19 | Embodiment 5 | 19 | 1 | 0 | 0 | 0.05 | I |
| Embodiment 20 | Embodiment 6 | 20 | 0 | 0 | 0 | 0 | I |
| Embodiment 21 | Embodiment 7 | 20 | 0 | 0 | 0 | 0 | I |
| Embodiment 22 | Embodiment 8 | 20 | 0 | 0 | 0 | 0 | I |
| Embodiment 23 | Cyclam | 19 | 1 | 0 | 0 | 0.05 | I |
| Embodiment 24 | Embodiment 9 | 20 | 0 | 0 | 0 | 0 | I |
| Embodiment 25 | Embodiment 10 | 20 | 0 | 0 | 0 | 0 | I |
| Embodiment 26 | Embodiment 11 | 20 | 0 | 0 | 0 | 0 | I |
| Embodiment 27 | Embodiment 12 | 20 | 0 | 0 | 0 | 0 | I |
| Comparative Example 2 | EDTA | 17 | 2 | 1 | 0 | 0.20 | II |

As shown in Table 6, all of the 0.5 wt of compositions for skin according to the present invention have grade I, which is a non-stimulating range, whereas the EDTA of Comparative Example 2 was evaluated to be grade II (weak irritation range), indicating that the skin irritation is higher than those of the compounds of the present invention.

INDUSTRIAL APPLICABILITY

The present invention relates to a dermal composition for protecting the skin from the external environment, and more particularly, to a dermal composition for effectively removing heavy metals and formaldehyde present in the skin and a composition comprising thereof.

The invention claimed is:

1. A pharmaceutical or cosmetic composition for protecting the skin from heavy metals and formaldehyde, comprising trientine of Formula (1a) or a salt thereof:

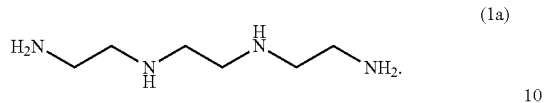
(1a)

2. The composition of claim 1, wherein trientine or a salt thereof is comprised in the range of 0.01 to 5.0 wt %, based a total weight of the composition.

3. The composition of claim 1, wherein the said composition is used as cosmetics, basic cosmetics, makeup cosmetics, cleansing cosmetics, shampoo or soap.

4. The composition of claim 1, wherein the said compound is used as a pharmaceutical auxiliary ingredient for hair loss treatment or skin related treatment by effective removal of heavy metals on the skin.

* * * * *